(12) United States Patent
Mujeeb-U-Rahman et al.

(10) Patent No.: US 11,224,714 B2
(45) Date of Patent: Jan. 18, 2022

(54) AND IMPLEMENTATION OF A LOW-COST BREATHING SUPPORT DEVICE

(71) Applicant: Ujala Technologies, Inc., Cincinnati, OH (US)

(72) Inventors: Muhammad Mujeeb-U-Rahman, Irvine, CA (US); Saad Pasha, Lahore (PK)

(*) Notice: Subject to any disclaimer, the term of this patent is extended or adjusted under 35 U.S.C. 154(b) by 0 days.

(21) Appl. No.: 17/316,705

(22) Filed: May 10, 2021

(65) Prior Publication Data

US 2021/0322715 A1    Oct. 21, 2021

Related U.S. Application Data

(62) Division of application No. 16/132,360, filed on Sep. 15, 2018, now Pat. No. 11,045,621.

(60) Provisional application No. 62/559,631, filed on Sep. 17, 2017.

(51) Int. Cl.
*A61M 16/20*    (2006.01)
*A61M 16/00*    (2006.01)
*A61M 16/06*    (2006.01)

(52) U.S. Cl.
CPC ...... *A61M 16/202* (2014.02); *A61M 16/0003* (2014.02); *A61M 16/0078* (2013.01); *A61M 16/06* (2013.01); *A61M 2016/0027* (2013.01); *A61M 2016/0033* (2013.01); *A61M 2202/0208* (2013.01); *A61M 2205/502* (2013.01)

(58) Field of Classification Search
CPC .......... A61M 16/0084; A61M 16/0078; A61M 16/0075; A61M 16/0081; A61M 16/006; A61M 16/0072
See application file for complete search history.

(56) References Cited

U.S. PATENT DOCUMENTS 6,155,257 A * 12/2000 Lurie ................... A61H 31/005
                                                    128/204.18
2020/0054520 A1 * 2/2020 Johnson ............... A61B 5/0022

* cited by examiner

*Primary Examiner* — Margaret M Luarca

(57) ABSTRACT

Respiratory diseases affect a large part of world population, especially in developing world. In this invention, we present a breathing support system to provide life-saving support to such patients. The system automates and regulates the use of a bag valve mask (commonly known as an ambu bag). The system uses mechanical actuators, sensors and a smart feedback control mechanism to automate and regulate the operation of the ambu bag to implement core functions of mechanical ventilation for life-saving applications. The system can also be used to provide better breathing support to newborns (e.g. to prevent hypoxia). The system can be used to save hundreds of thousands of lives in the developing world, in emergencies and during transportation globally.

14 Claims, 21 Drawing Sheets

AND IMPLEMENTATION OF A LOW-COST BREATHING SUPPORT DEVICE

CROSS REFERENCE TO RELATED APPLICATIONS

The present application is a division of U.S. application Ser. No. 16/132,360, filed Sep. 15, 2018, entitled "DESIGN AND IMPLEMENTATION OF A LOW-COST BREATHING SUPPORT DEVICE," currently pending; which claims the benefit of U.S. provisional application No. 62/559,631 entitled A SMART, LOW-COST HARDWARE AND SOFTWARE SOLUTION FOR A PORTABLE VENTILATOR, filed on Sep. 17, 2017, which is incorporated herein by reference in its entirety.

TECHNICAL FIELD OF THE INVENTION

The present invention relates with the design and implementation of a medical device to assist patients with breathing difficulties.

BACKGROUND

Respiratory diseases affect a significant portion of world population, especially in the developing world due to environment. For example, around 71,000 children die of pneumonia annually in Pakistan. Similarly, chronic obstructive pulmonary disease (COPD) affects 2.1 percent of Pakistani population aged 40 years and above [1]. Almost 33% of these patients are hospitalized due to their COPD symptoms while 27% of them visit emergency room each year. Similarly, nearly 20 million adult Pakistanis are already suffering from asthma and it is increasing at an alarming rate of 5% annually [2]. Around twenty to thirty percent of these patients are children between 13 and 15 years of age [2]. Furthermore, many patients (mostly aged and children) get seasonal respiratory diseases and need acute treatment in emergency conditions. Last year alone, dozens of children died due to unavailability of ventilators in hospitals across Pakistan alone. Low-cost and easy to repair life-saving devices can provide a solution to such large-scale problems [3].

A mechanical ventilator is often required to treat patients with respiratory problems [4]. This treatment can be acute or chronic (for months) depending upon patient condition. According to healthcare standards, hospitals should have at least 50% of beds with ventilators always available for emergency patients 151. Furthermore, these devices should be available at all levels i.e. districts and tehsils so that patients can be treated closer to their family without having to travel long distance. However, this number becomes too large for dense population in many parts of the developing world. Furthermore, most of the public hospitals don't have the infrastructure to provide such facilities to the large population. Moreover, the current ICU ventilators are big and are designed for developed world hospitals (require extensive hospital infrastructure and trained staff) and aren't optimized for developing and underdeveloped countries for large scale use. There are some smaller units available, however those devices are still expensive and difficult to maintain in large numbers.

In consideration of difficulties associated with access to life-saving ventilators in many areas of developing world, we have developed a smart, affordable, and accessible breathing support device that can act as an alternative to a traditional hospital ventilator for life saving cases and can be maintained in low-resource settings. This new device will not only provide the function of a life-saving ventilator but will also be equipped with remote monitoring capabilities allowing for a smarter use and data collection and decision-making process. The smart wireless interface will allow real-time data collection and prediction to match population needs and resources in an efficient manner. The device uses the approved Ambu bag (also known as Bag Valve Mask) technology for easy adoption by the medical community. We have successfully implemented our system and have tested it on human patients under the supervision of senior doctors. This system has the potential to save hundreds of thousands of lives throughout the world in emergencies and during transportation.

SUMMARY

A mechanical ventilator is often required to treat patients with respiratory diseases and can save lives if readily available [3]. These devices should be available at all levels so that patients can be treated closer to their homes without having to travel long distance. Current state-of-the-art ventilator systems are expensive and difficult to use (require infrastructure and trained staff) and hence have proven to be inefficient for the scale of problem [6]. Experts believe that local maintenance and optimization of ventilator systems is the ultimate solution for these problems [7].

Traditional medical instruments are not designed to have wireless connectivity for safety and simplicity reasons. However, current wireless protocols have performance characteristics acceptable and allowed by regulatory authorities and hence wireless connectivity has started to become a standard in medical device community [8]. Hence, our goal is to develop smart systems that can be seamlessly integrated with other information and communication technologies and thus provide real-time monitoring and usage information without having to retrofit other devices. The data gathered can be analysed for trend analysis that would make the healthcare system simpler, smarter and scalable.

Local development of important healthcare solutions can provide sustainable solution to large scale problems such as the respiratory disorders in developing countries [9]. In some cases, such systems can be used in developed world as well for emergency situations [10]. Although efforts have been made in realizing low-cost portable ventilators [11], such systems have been limited to academic exercises and have not resulted in real systems that can be used in actual clinical applications.

The specific ventilator design presented in this invention is built upon existing breathing technologies used by the medical community to facilitate adoption. It uses a Bag Valve Mask (BVM) that, in under-served communities is used manually by patient's caregivers for hours, or days and sometimes weeks and is clearly not an efficient and reliable solution to provide breathing support to patients who are too sick to maintain their own respiration. However, its use is acceptable clinically and it has proven to be a life-saving resource when more advanced ventilators are not available. Present invention removes the limitations associated with use of the BVM (also known as the Ambu bag) manually by automating its operation and by using sensors to regulate such use to make is safer and more effective.

The invention presented here describes a novel breathing support device design using a simple architecture that conforms to the medical safety and efficacy requirements for life-saving applications. This is achieved by realizing an efficient feedback control mechanism based upon pressure and flow sensors [12]. We use accurate pressure and flow sensors with proper specifications to measure system state, using similar standards that are used in hospital ventilator systems [13].

The presented device is designed to be powered by AC current or with a battery which allows for long-term field use where AC power may be unavailable or intermittent. This also allows for bedside use in hospital settings where AC power may not be available for all devices during epidemic or emergency conditions or use in emergency vehicles.

The proposed system uses a modular design which allows low-cost and simpler maintenance. The system has an internal diagnostic capability to determine which module (s) need replacement during maintenance. The minimizes need for expensive diagnostic instruments and repairs.

In a typical operation, the system works in Assist-Control (AC) mode in which a breath cycle may be started by patient or otherwise by internal controller based upon Inhalation to Exhalation Ratio (I:E) and number of breaths required per minute. After breath cycle starts, continuous monitoring of air flow rate and tidal volume is done using different sensors. After providing the tidal volume set by the user, exhalation cycle starts, and system again wait for patient or internal timers to trigger next inhalation cycle.

Breath flowrate, delivered-volume and lung-pressure is measured just outside the patient mouth via two sensors; an air flowrate sensor (99) and a pressure sensor attached to the small opening (100). Motor input voltage which is controlled by Pulse width Modulation PWM, depends on the feedback from these two sensors. Breath flowrate and delivered air volume is measured via medical grade 6 to 24-Volt MEMS based hot-wire air flow sensor (99). Flow sensor range is about −50 liters per minute (LPM) to +50 liters per minute (LPM). The range −50 LPM to 0 LPM (i.e. flow direction is from patient to device) is to measure the exhalation flowrate and volume whereas the range 0 LPM to +50 LPM (i.e. flow direction is from device to patient) is to measure inhalation flowrate and volume. Sensor electrical output could be analog or digital I2C and standard medical mechanical interfaces are easily available.

Breath pressure is measured by the medical grade MEMS based pressure sensor attached to the small opening (100) via any means e.g. a small plastic tube or direct interface. Pressure sensor range is about −10 cmH2O to +70 cmH2O. The pressure range −10 cmH2O to 0 cmH2O is used to detect the pressure drop generated by the patient's attempt for inhalation. Special ventilator-oriented MEMS based medical grade flow, pressure, humidity and temperature sensors all built in one single package with standard medical interfaces can be used to simplify the sensing unit (SU).

Figure 9:
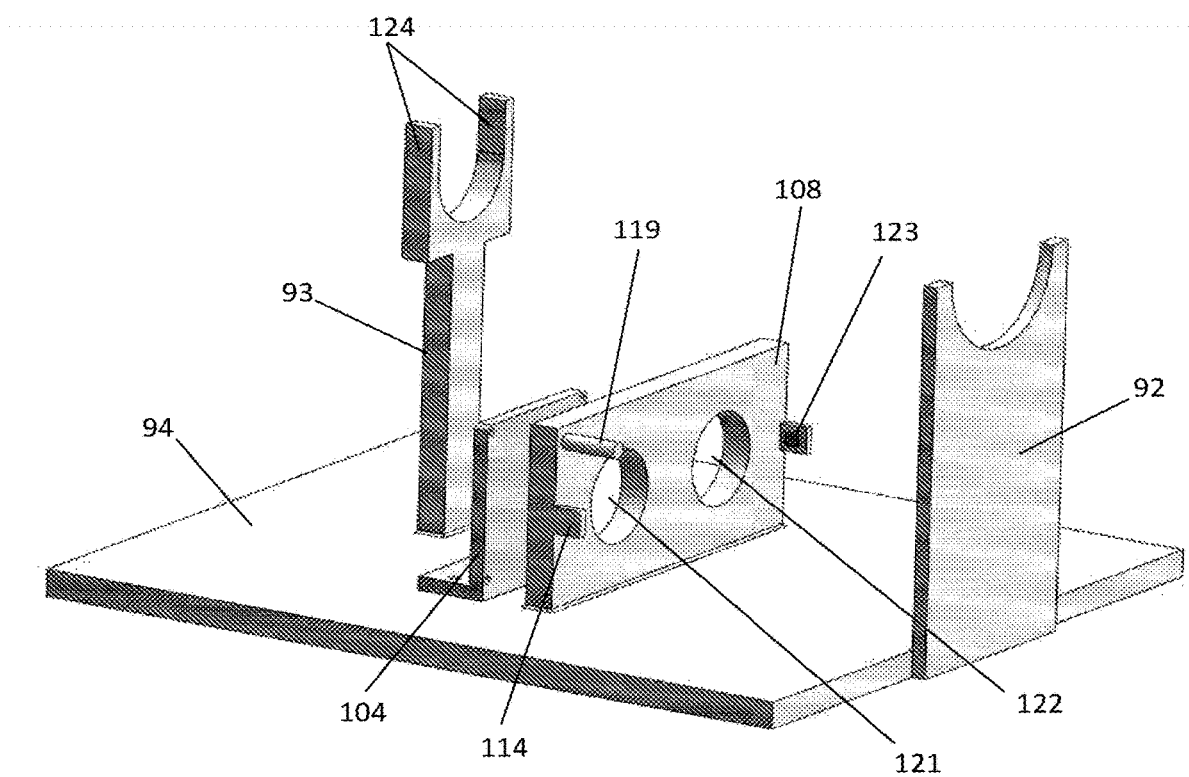
Figure 11:
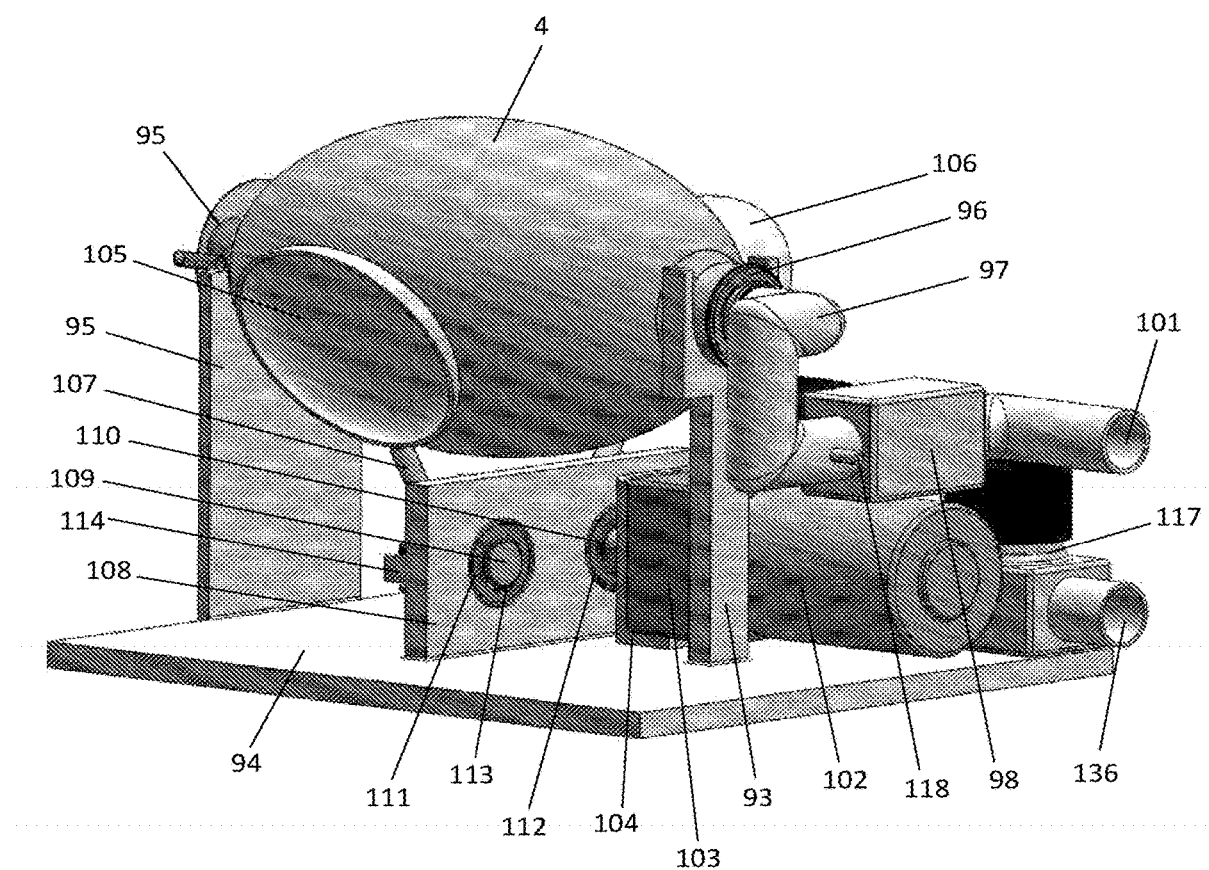
Figure 12:
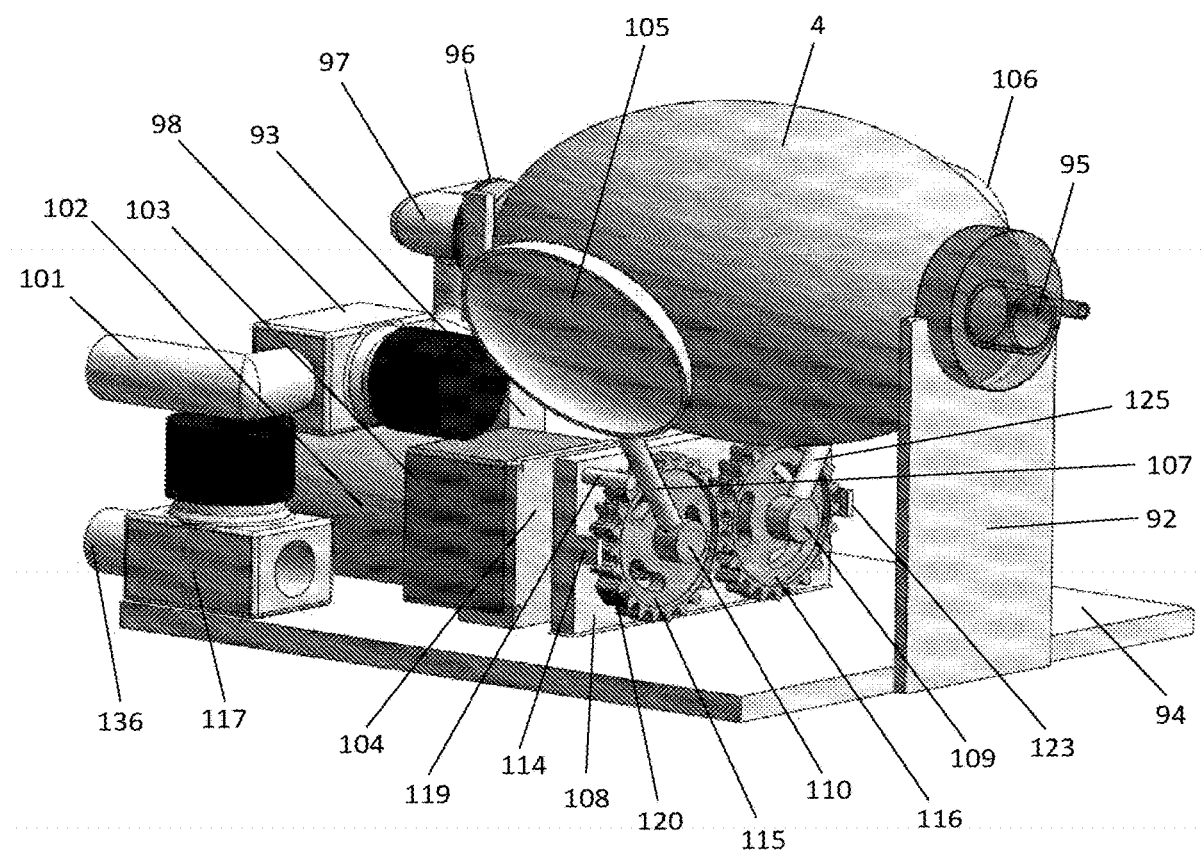

FIG. 9 shows the base mechanical structure of the ventilator which holds all of the electromechanical structures. There is a 10 mm thick base plate (94) on which all structure and components rest. This plate is a part of outer body of the ventilator and could me made with any medical grade material like Teflon, acrylic, aluminum, or PVC. Size of base plate (94) is 25×28 cm, where 28 cm is along the pillars situated on the base plate (94). There are two pillars situated on the base plate used to hold the Bag Valve Mask BVM (4) (FIG. 11). One pillar acts as back support (92) and other pillar acts as front support (93). Back support (92) may be 5-10 mm thick depending upon the thickness of outer covering body which used to cover the ventilator's electromechanical structures. Its width is 82 mm and depends on the size and diameter of BVM inlet (4) (FIG. 12). The back-support width is larger than the diameter of inlet (95) (FIG. 12) from both sides by 10 mm. Front support (93) is 10 mm thick and has width of 20 mm and can be up to 50 mm. This support holds BVM as well as piping circuitry (97) (FIG. 11). The distance between two supports (92) and (93) is 20 cm, equals to the length of the BVM (4) (FIG. 11). Front support's width is larger than the outlet (96) of BVM by 5 mm each side (FIG. 11).

The diameters of semicircles on back (92) and front (93) support are 62 mm and 42 mm respectively and depends on the diameters of inlet (95) and outlet (96) of BVM (4) (FIG. 12). The semicircle of front support (93) has long arms (124) of 2 cm each to hold the BVM. Height of both supports from their centers of semicircles is 12 cm.

There is a plate namely gear plate (108) situated on the base plate with two holes (121) and (122). Gear plate (108) holds two meshing gears (115) and (116) (FIG. 12) via two ball bearings (111) and (112) (FIG. 11). These two ball bearings sit in the two holes (121) and (122) in the gear plate (108). In a typical case, the thickness of gear plate (108) is about 10 mm and depends on the thickness of the ball bearings used. In a typical case, the dimension of gear plate (108) is 7 cm-by-13.5 cm. There is one round extrusion (119) from the gear plate of 8 mm diameter and 3 cm length and used as a mechanical stopper or limiter (FIG. 12). This mechanical stopper (119) can be made as integral part of base plate or by simply inserting a nut in the base plate.

There are two small seats (114) and (123) of size 1×1 cm at the both ends of gear plate with 3-5 mm thickness. These two seats (114) and (123) are used to hold/adhere Hall Effect Sensor's ICs to electronically detect the extreme positions of two meshing gears (FIG. 12) by sensing the magnets (120) attached to each gear (FIG. 12). The positions of seats are exactly in the center of the gear plate (108) when measured from the base plate (94). There is one metallic or nonmetallic support (104) for motor. Its size depends on the motor being used. It must be placed such that motor output shaft can be coupled with one of the gear.

Figure 10:
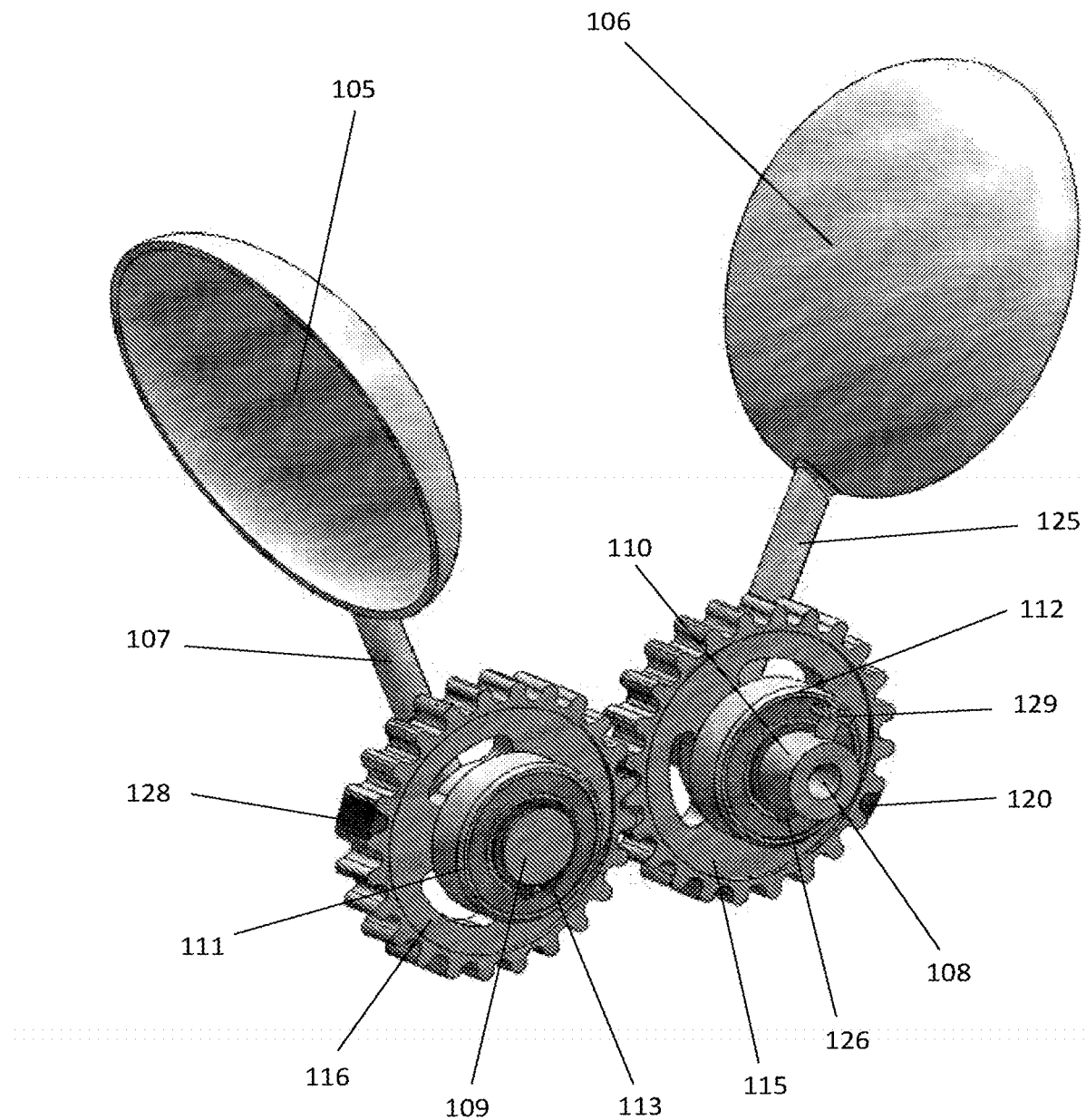

FIG. 10 shows one implementation of the MAU. A pair of mechanical jaws (105) and (106) is used to press the BVM.

Jaws are spherical in shape and have smooth surface made with rust free hard material e.g. stainless steel. Diameter of a jaw can be up to 20 cm depending on the size and shape of the BVM. Each jaw (105) and (106) is connected to a rod (107) and (125) made with same material e.g. stainless steel. Each rod is connected to gear shaft (109) and (110) and gears (115) and (116). Machining or welding can be used to build this assembly. Diameter of each gear shaft (109) and (110) is 17 mm and depends on the internal diameter of the gears. Length of the gear shaft (109) is 35 mm and that of (110) is 40 mm. The size of the gear shaft depends on the diameter of jaw's rods, thickness of the gears, thickness of the ball bearings and thickness of mechanical metallic locks (113) and (126). Mechanical metallic locks are used to hold the gear shaft from one side of ball bearings (111) and (112), the other side is held by the welded gears. The internal diameter of metallic locks is 15 mm and depends on the diameter of gear shaft. Central distance between the centers of gears can be up to 80 mm. Gears are made with mild steel and can be made with any other medical grade material including polymers. Depending upon the size of BVM and spherical spoons, gears size and internal distance between the gears can be changed. Gear tooth should be capable of transferring 80-120 kgcm of torque.

Both gears are held by gear plate (108) via corresponding ball bearings (111) and (112). Their internal diameter is 17 mm and depends on the diameter of gear shafts (109) and (110). Their outer diameter is 35 mm and thickness is 10 mm. Depending on the diameter of gear shafts, size of ball bearings can be changed. The 8 mm hole (127) in 40 mm gear shaft (110) is to insert motor shaft. Diameter of hole (127) depends on the diameter of motor shaft. A nut (129) is used to tighten the motor shaft with gear shaft (110). Through this coupling, motor can drive the mechanism to press the BVM to deliver a breath. There are two magnets (120) and (128) attached to each gear to give signals to Hall Effect Sensors (114) and (123) to detect extreme positions.

FIG. 11 shows a typical mechanical design of the ventilator. Gas Volume Generator GVG or Bag Valve Mask BVM (4) is the main component of this system and is universally accepted as a hand-held manual resuscitator. Usually BVM is made with Silicone. From its both ends, BVM is supported by two supports, back support (92) and front support (93). At the inlet (95) of BVM, there is a built-in one-way valve which lets air in when BVM expands. Outlet of the BVM (96) is supported by the front support (93) and attached to a piping circuitry (97) through which the air goes out from the device. Outer diameter of piping circuitry is 25 mm and depends on the inner diameter of outlet (96) of the BVM. Internal diameter of piping circuitry is between 15 mm to 22 mm, which are medically used diameters for breathing circuits. Piping circuitry can be made using any medical grade material e.g. Teflon, Acrylic or PVC or can be made using berating-circuit tubes (83) after cutting them in small lengths. A plunger-type, 12 or 24-Volt solenoid operated ON-OFF inhalation valve (98) with 10 mm to 15 mm orifice diameter is used to cut-off the air flow when required volume is delivered by the BVM. It may be used to build pressure, which is measured by a pressure sensor attached to the port (118), at the start of breath to achieve some of the ventilator flow and pressure waveforms. This inhalation solenoid valve also act as a one-way valve allowing air to go from BVM to outlet port (101) and never let air to return to BVM. If exhaled breath reaches the BVM, it will contaminate the BVM which either will require a new BVM or to sterilize the old BVM to use the device again. The pressure bearing value of solenoid valve is about 50-70 cmH2O.

Figure 1:
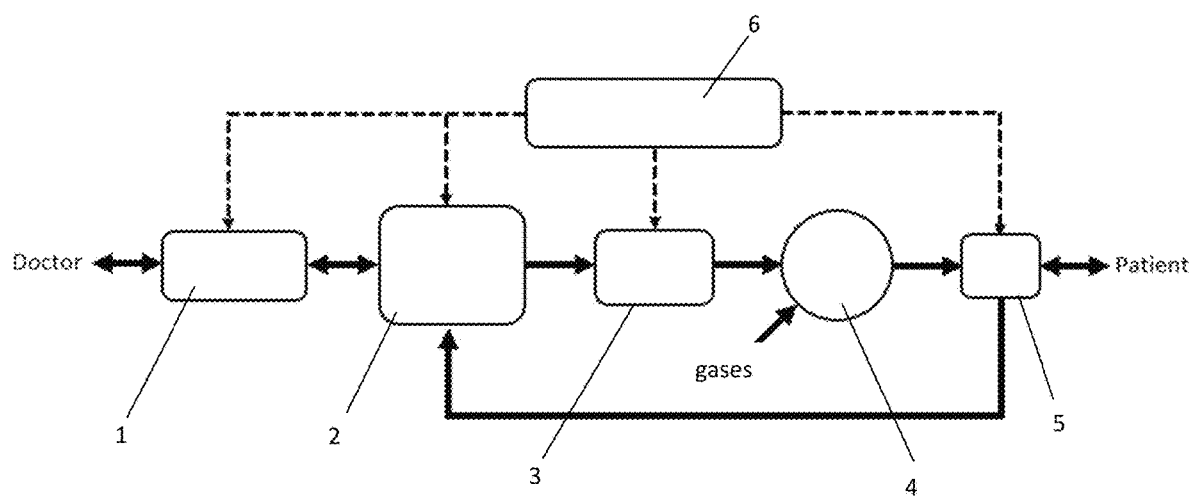
FIG. 1 shows the high-level block diagram illustrating the hardware design of the ventilator system. It has a user interface (1) i.e. a human-machine interface (HMI) where a doctor or nurse can enter required breathing parameters and in return can see the resultant parameters. The system has a system control unit (CU) (2) which takes input from user interface (1) and then controls the mechanical actuation unit (MAU) (3). The MAU (3) actuates the gas volume generator (GVG) (4) which has the mixture of gasses for current breath. The breath generated by the GVG (4) passes through a sensing unit (SU) (5). The SU (5) is used for feedback control in the CU (2). After the SU, the gas mixture reaches the patient. Additionally, there could be a humidity and temperature control unit between the SU and the patient to adjust humidity and temperature of the gas mixture. A power management unit (PMU) (6) takes input from AC mains or from batteries (in the absence of AC mains) and distributes the power to every unit according to its requirement. The PMU (6) is also responsible to switch from AC mains to batteries, and vice versa, uninterruptedly.
Figure 2:
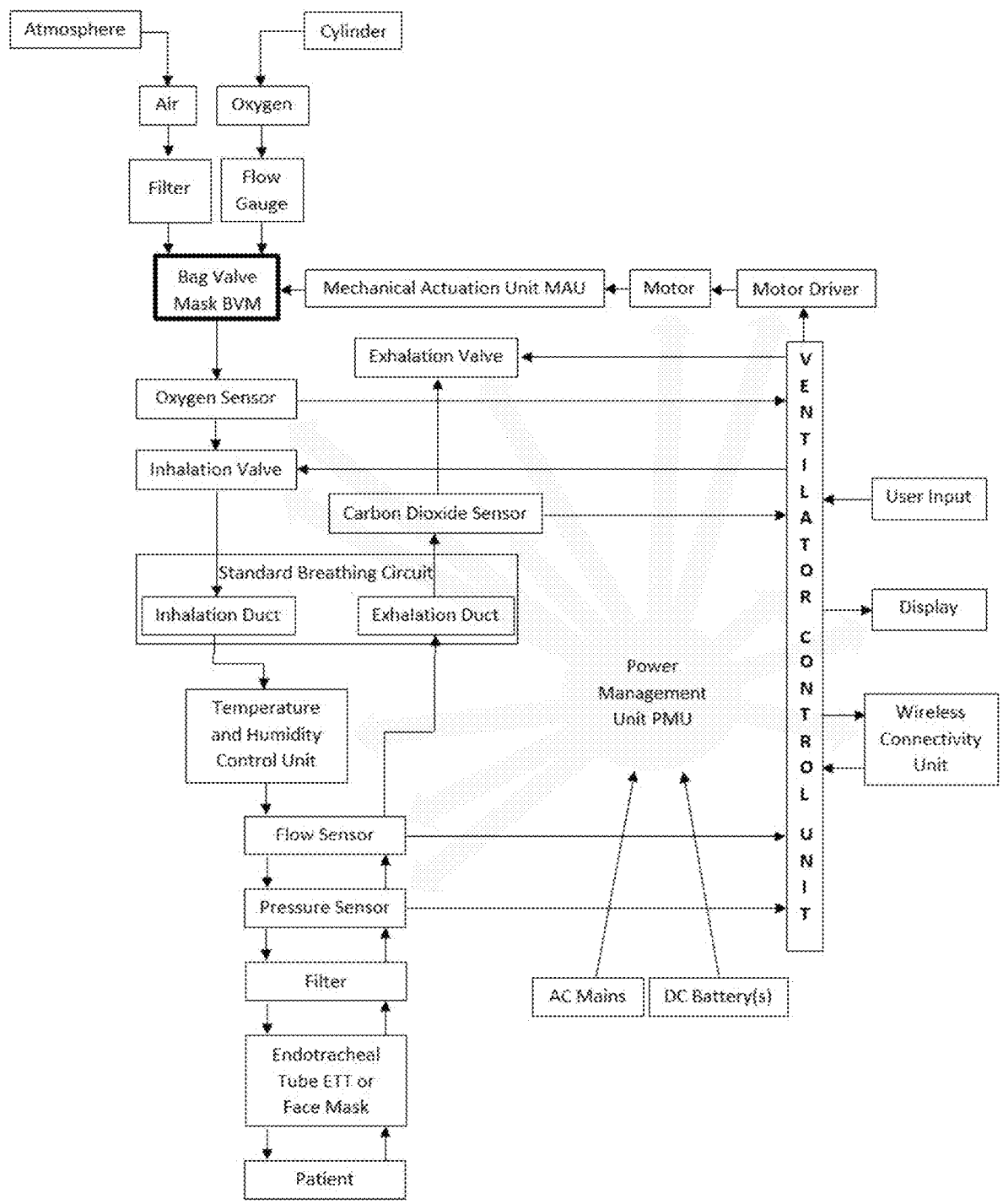
FIG. 2 shows the detailed hardware design of the system. The atmospheric air passes through a filter and enters the GVG via its air inlet. Oxygen from a cylinder enters the GVG via its oxygen inlet. Oxygen flow is controlled via a manual flow gauge attached to the oxygen cylinder or oxygen port. An air-oxygen mixture or air-oxygen blender can also be used to control the concentration of oxygen in delivered breath. A typical example of a GVG is a bag valve mask (BVM). When the BVM is compressed via MAU, which is actuated by a motor, the air goes through an optional oxygen concentration sensor, inhalation valve and the out to the inhalation duct of standard medical breathing circuit. An optional temperature and humidity controller, usually as separate unit, can also be installed in inhalation duct. The air passes through a flow rate sensor and a pressure sensor just outside the patient's mouth for accurate measurements. After flow and pressure sensor, air passes through a filter and enters patient's lungs via a face mask or an endotracheal tube (ETT). The exhaled air passes through the same flow rate and pressure sensor and enters exhalation duct of breathing circuit. Exhalation duct can have an optional carbon dioxide concentration sensor to monitor exhaled carbon dioxide. At the end of exhalation duct there is exhalation valve. The exhalation valve stays closed during inhalation. All sensor outputs and user input (e.g. via a keypad or knob) are provided to the CU (typically a microcontroller) which then controls the valves and motor operation (via a motor driver) and displays the breath parameters on a display (e.g. LCD).
Figure 3:
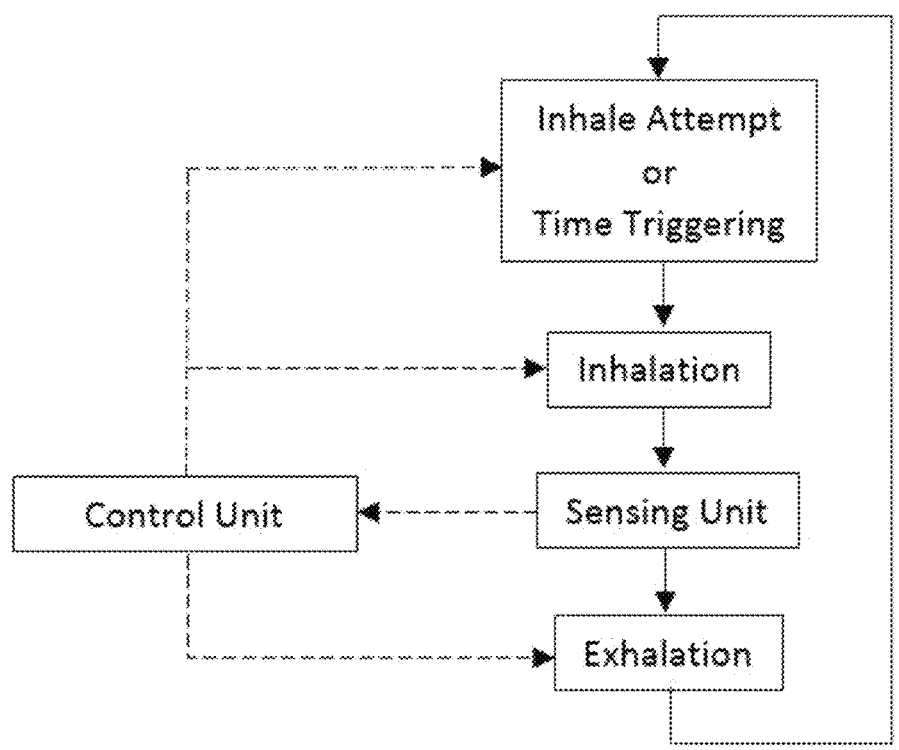
FIG. 3 shows the high-level diagram of the proposed decision-flow architecture. Breath cycle starts by patient inhalation attempt or by internal timers based upon breaths per minute (BPM) required. During inhalation, flow rate, tidal volume and peak inspiratory pressure is monitored to minimize ventilator induced lung injury (VILI). After delivering set tidal volume or achieving set pressure in given inhalation time, exhalation starts.
Figure 4:
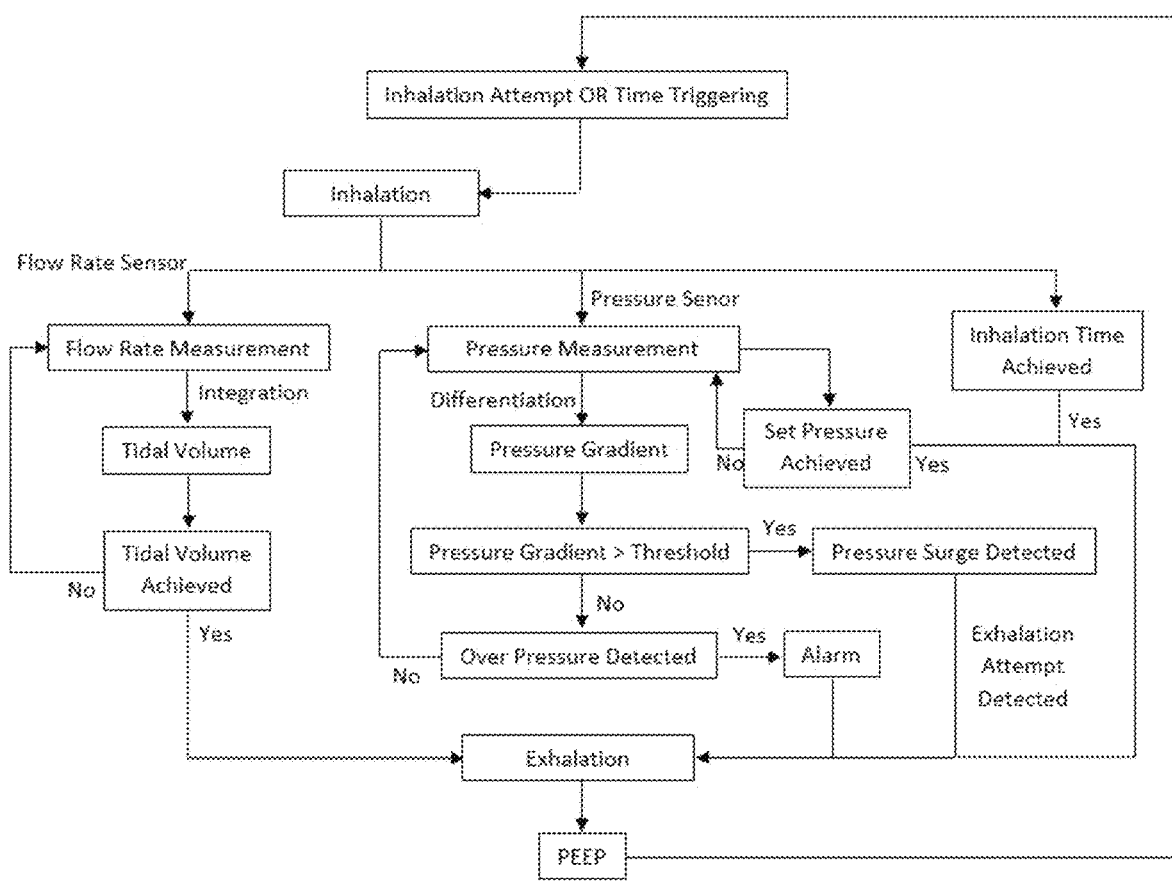
FIG. 4 is the block diagram illustrating the detailed decision-flow architecture (also termed as software architecture). The CU (e.g. microcontroller) detects the patient's inhalation attempt and starts the breathing cycle. Inhalation can also be started on the base of internal timers of the microcontroller. Internal timer is set according to respiratory rate i.e. number of breaths required in a minute. During the inhalation cycle, breath is continuously monitored and measured by different sensors, the main two sensors are flow rate sensor and pressure sensor. If volume-targeted ventilation is used, inhalation ends when breath volume is achieved, where breath volume is calculated by integrating flow rate. If pressure-targeted ventilation is used, inhalation ends when breath pressure is achieved, where breath pressure is measured by pressure sensor. Inhalation can also be terminated by the internal timers according to the inhalation to exhalation ratio (I:E) set by the doctor. Software architecture also provides the safety by detecting patient's exhale attempt while system is delivering a breath. If during inhalation, patient tries to exhale, system will detect the pressure surge and will allow patient to exhale immediately. Similarly, during inhalation, if peak pressure crosses the allowable peak pressure set by the doctor, system will exhale immediately and turn on the alarm. After exhalation is completed, Positive End Expiratory Pressure PEEP is maintained by the controller and then system go back to start the breath cycle again.
Figure 5:
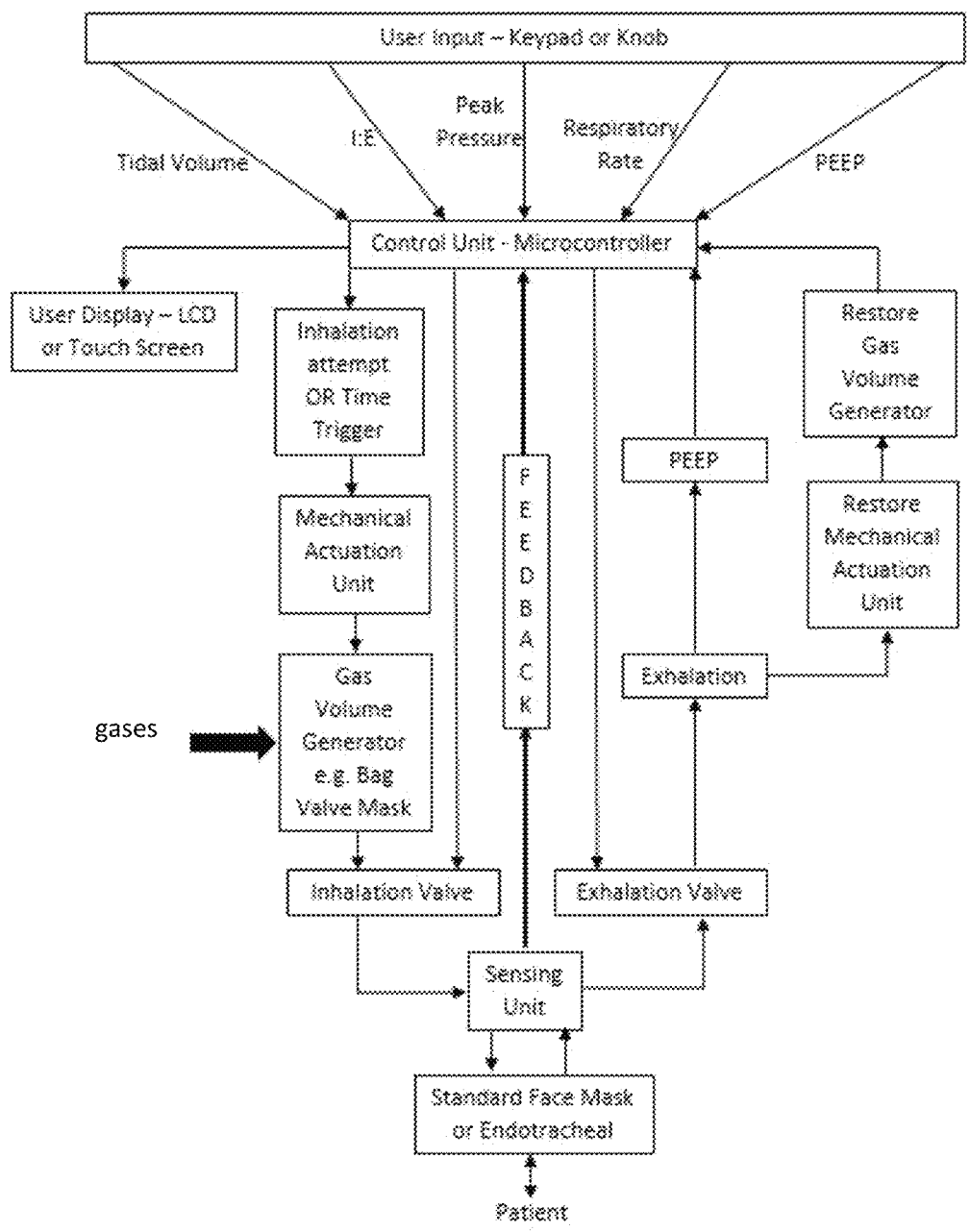
FIG. 5 illustrate high level operation of the system. At the beginning, the doctor enters required breath parameters (respiratory rate, volume, pressure, etc.) by user interface. The CU then controls patient's respiration depending upon set parameters. The CU starts inhalation by actuating the MAU via actuating a motor. The CU controls breath parameters by controlling motor operation via Pulse Width Modulation (PWM). During inhalation, the CU keeps inhalation valve open whereas it keeps exhalation valve closed. As soon as required volume is delivered or set pressure is developed, the MAU stops, and inhalation valve is closed. After an optional time delay, exhalation starts. During exhalation, microcontroller keeps exhalation valve open and keeps monitoring pressure to maintain PEEP. As soon as pressure drops to set PEEP pressure, microcontroller closes the exhalation valve. During exhalation and PEEP maintenance, microcontroller restore the MAU as well as GVG, both in parallel to exhalation and PEEP maintenance. After that, microcontroller starts the next cycle.
Figure 6:
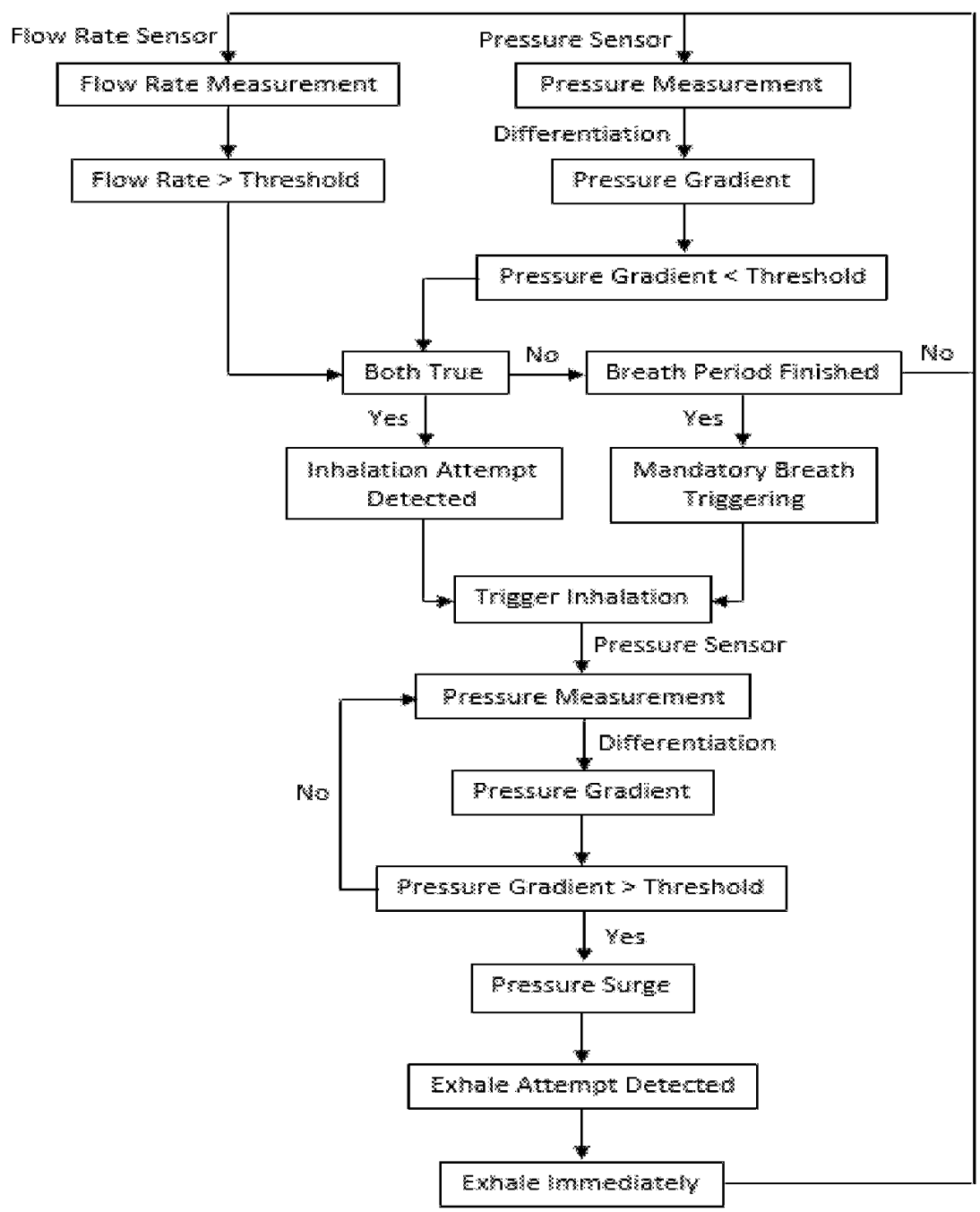
FIG. 6 illustrates the synchronization scheme of the presented system's breathing cycle with that of the patient's. Breathing cycle can be triggered in two ways, patient-triggered and time-triggered. Time triggering depends upon number of breaths per minute required. Patient-triggering depends on patient, when patient wants to take a breath. Pressure-drop and flow rate surge is continuously measured to detect patient inhale attempt. As the pressure becomes less than a threshold or flow rate become greater than the threshold, patient-triggered inhalation starts. During inhalation, pressure is again continuously measured and differentiated to stop inhalation if patient attempts exhalation. If pressure gradient becomes greater than a threshold, pressure is detected which is a sign of positive pressure by patient i.ie exhalation. So, the system exhale immediately.
Figure 7:
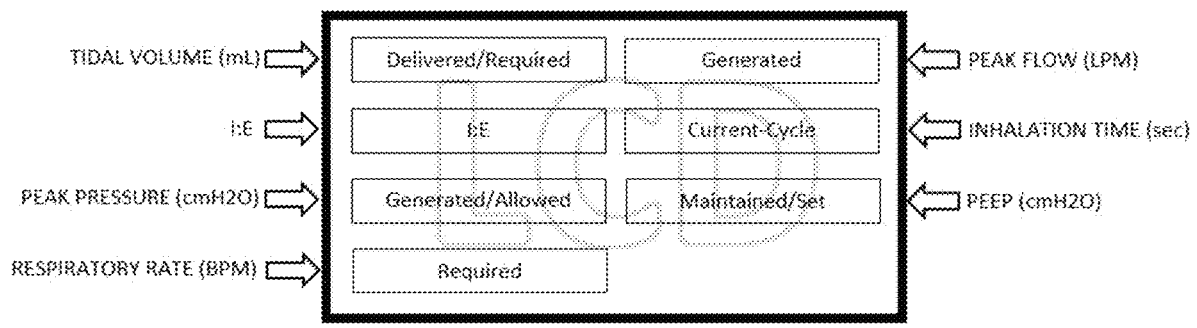
FIG. 7 represents the display used for the ventilator. An LCD is used to display different ventilation parameters including but not limited to Tidal Volume, Inhalation:Exhalation Ratio (I:E), Peak Pressure, Breaths per Minute, Peak Flow Rate, Inhalation Time and PEEP. A touch screen can also be used, and breath waveforms can also be shown including all above mentioned breath parameters.
Figure 8:
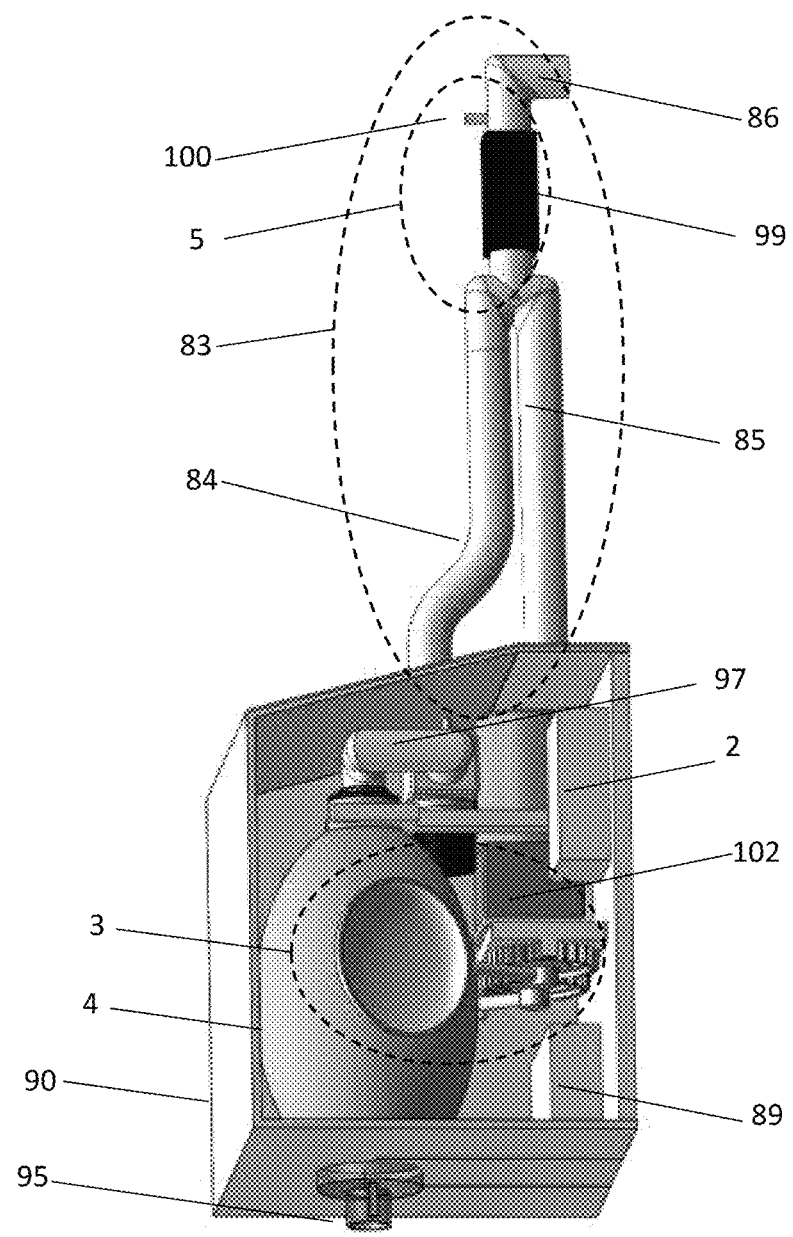
FIG. 8 gives an overview of the device structure; the detailed design and description of each part is provided in later figures. The internal structure of the device is covered by a medical grade plastic, metal, or polymer body (90). A Bag Valve Mask BVM (4) is the main component of the device and acts as gas volume generator GVG (4) (FIG. 1) or a source of air-reservoir for mechanical breaths. There is a one-way valve (95) which acts as air-inlet to the BVM (4) and hence air-inlet to the device. This one-way valve (95) is a built-in part of every Bag Vale Mask BVM (4). In the absence of main power supply, device is powered by a 12V or 24V maintenance-free sealed battery (89) like Lead-Acid, Li-Ion and Li—Po. Bag Valve Mask BVM (4) is compressed by a mechanical actuation unit MAU (3) actuated by a DC geared motor (102) whose input voltage is controlled by control unit CU (2), typically a microcontroller and its electronics, in a feedback manner. Feedback is taken from sensing unit (5) comprised of two sensors just outside the patient mouth; flowrate sensor (99) and pressure sensor attached to the small opening (100). Upon compressing Bag Valve Mask (4) by mechanical actuation unit (3), air goes out from the system through the internal piping circuitry (97) which contains a pressure sensor, solenoid operated ON-OFF valve and a pressure relief valve (explained in later figures). This air reaches the patient mouth which is connected at the outlet (86) via inhalation limb (84) of standard medical vent-to-patient tube. Inhaled air is then exhaled by the exhalation limb (85) of the standard medical patient-to-vent tube. These two tubes (84) and (85) collectively called breathing-circuit (85) and available as one unit. Breathing circuits are made with different materials and may be disposable or reusable, and always are flexible. At outlet (86), patient can be interfaced via an Endotracheal Tube ETT or a face mask.

At the end of internal piping circuitry (97), there is a standard ventilator interface (101) which connects the ventilator outlet port to the patient via breathing circuit's (83) (FIG. 8) inhalation limb (84) (FIG. 8). The exhalation limb (85) (FIG. 8) is connected to the inlet port (136) of the device. The Inlet port (136) is connected to a plunger type 12/24V solenoid operated ON-OFF valve (117). This is called exhalation valve or PEEP valve which is used to control the Positive End-Expiratory Pressure PEEP. PEEP is simply the pressure needs to be maintained in the lungs after exhalation and its typical value is between 0 cmH2O to +10 cmH2O.

During inhalation, inhalation solenoid valve (98) gets opened and the exhalation solenoid valve (117) gets closed allowing air to flow in the lungs. After completing breath, inhalation stops and inhalation solenoid valve (98) gets closed whereas exhalation solenoid valve (117) gets opened allowing air to go to the atmosphere. During exhalation, exhalation solenoid valve (117) gets closed as soon as the lung pressure being measured by the pressure sensor at the small opening (100) (FIG. 8) becomes equal to the set value of PEEP. Mechanism of breath delivering is achieved by pressing the BVM via Mechanical Actuation Unit MAU, explained in FIG. 10, whose actuating part is a DC geared motor (102) with a gear box (103) and supported by a metallic support (104). Any long-life DC geared motor with 20-200 kgcm torque, 5-100 RPM, 12/24-Volt input voltage with 25-60 Watt input power, small sized and lightweight can be used.

FIG. 12 shows another view of a typical implementation of the device. Bag Valve Mask BVM (4) is supported by two supports, back support (92) and front support (93). Both supports are connected to the 10 mm thick base plate (94). At the inlet of BVM, there is a built in one-way valve (95) which lets air in when BVM expands. Outlet of the BVM (96) is attached to a piping circuitry (97) through which the air goes out of the device. In piping circuitry, there is one plunger-type solenoid operated ON-OFF valve (98) which is called inhalation valve. At the end of piping circuitry, there is a standard medical interface (101) which is the device inhalation port and connects the device to the patient via breathing circuit (83). Device exhalation port (136) is connected to breathing circuit's (83) (FIG. 8) exhalation limb (85) (FIG. 8). Exhalation port (136) is connected to a 12/24 volt solenoid operated ON-OFF valve (117) or PEEP valve. Mechanism of breath delivering is achieved by pressing the BVM via Mechanical Actuation Unit MAU, whose actuating part is a DC geared motor (102) with a gear box (103) and supported by a metallic support (104). Motor press the Bag Valve Mask BVM by two mechanical jaws (105) and (106). Each spherical jaw is mounted on rods (107) and (125).

Figure 13:
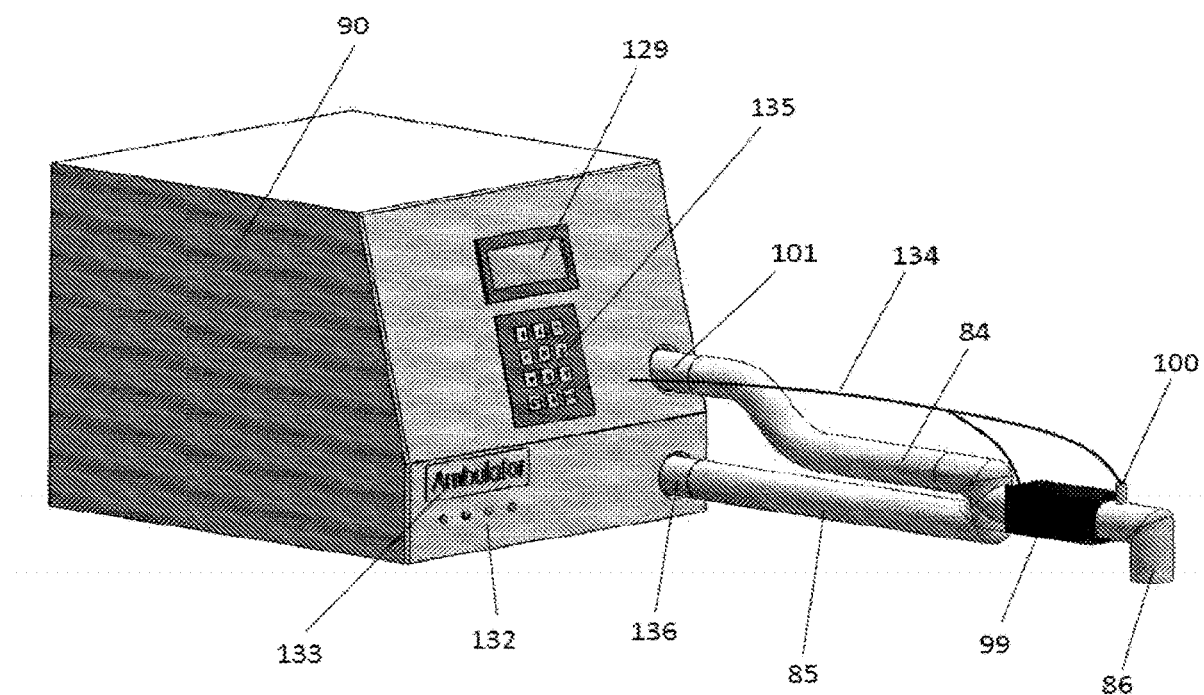

FIG. 13 represents the actual ventilator after all the designs are implemented. Bag Valve Mask BVM or Gas Volume Generator GVG (4), Mechanical Actuation Unit MAU (3), Motor and all other parts are enclosed in the enclosure/body (90). Enclosure front has user interface (1) consisting of an LCD (135) and a keypad input (130). A touch screen with a simple knob like conventional ICU ventilators can also be used. The enclosure (90) also has some indictor LEDs (132) indicating Power, Main, ON and Battery. A typical device name (e.g. The "Ambulator") is also displayed (133) on the enclosure (90). Device inhalation port (101) is connected to the inhalation limb (84) of standard medical breathing circuit. Device exhalation port (136) is connected to the exhalation limb (85) of standard medical breathing circuit. The breath from the device reaches to the patient mouth, which is attached at the patient outlet (86) at the end of breathing circuit via Endotracheal Tube ETT or a mask, through device inhalation port (101), inhalation limb (84) of breathing circuit, flowrate sensor (99), pressure sensor (100), one or two filters (131) and L-shaped patient outlet (86). Exhalation air passes through the pressure sensor (100), flowrate sensor (99), exhalation limb (85) of breathing circuit and exhalation port (136) of the device. After entering exhalation port, air passes through the PEEP valve and then to atmosphere. The set of wires (134) going along the breathing circuit, is to power up flowrate (99) and pressure (100) sensor and to take their signals to the control unit (2) present in the device. Breathing circuit (83), filters (131), patient outlet (86) and ETT all are available in each and every hospital. They all are just needed to attach to the device in the same manner as to a conventional ICU ventilator. Flowrate sensor (99) and pressure sensor (100) are needed to attach to the breathing circuit just like D-Lite tube used in conventional ICU ventilators to measure flowrate, volume and pressure.

Figure 14A:
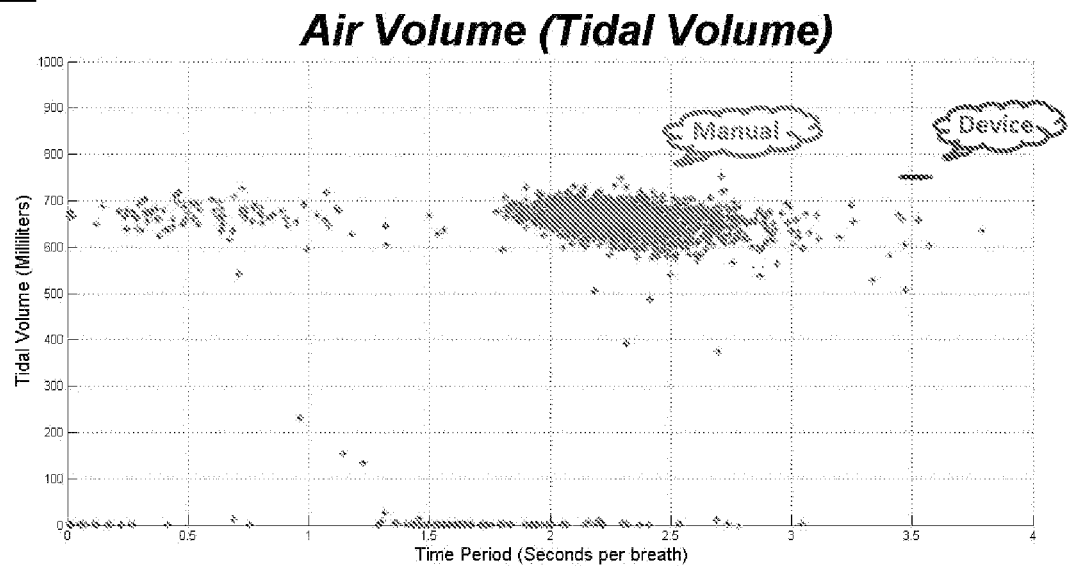
Figure 14B:
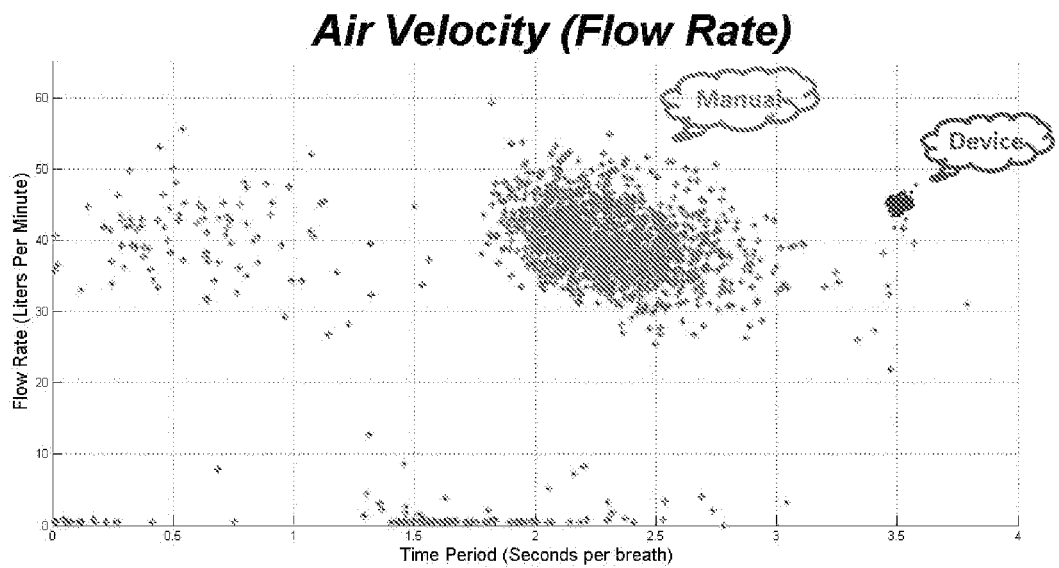
Figure 14C:
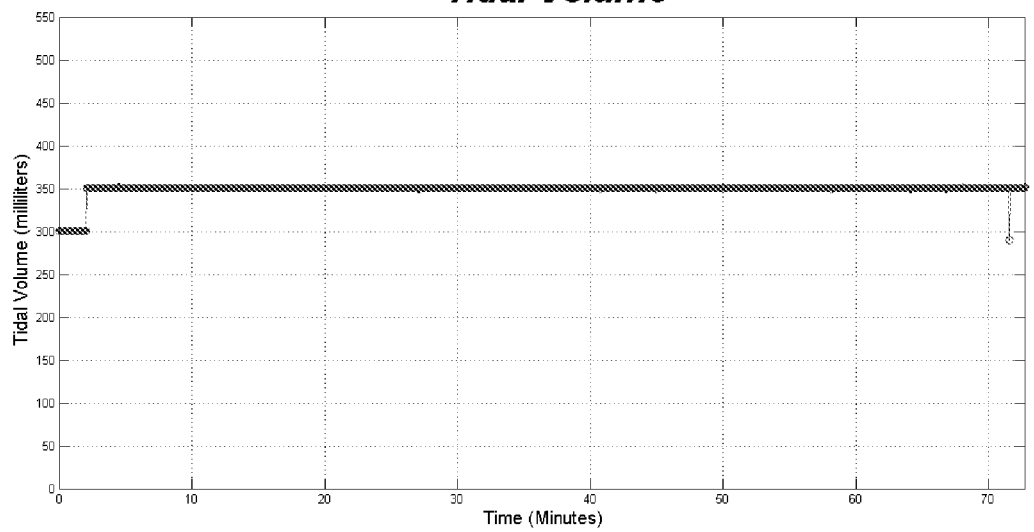
Figure 14D:
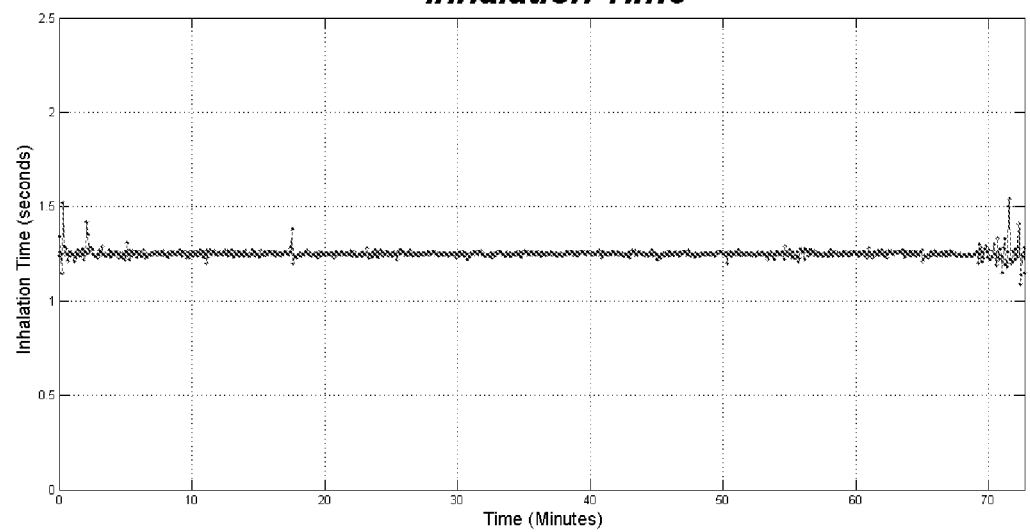
Figure 14E:
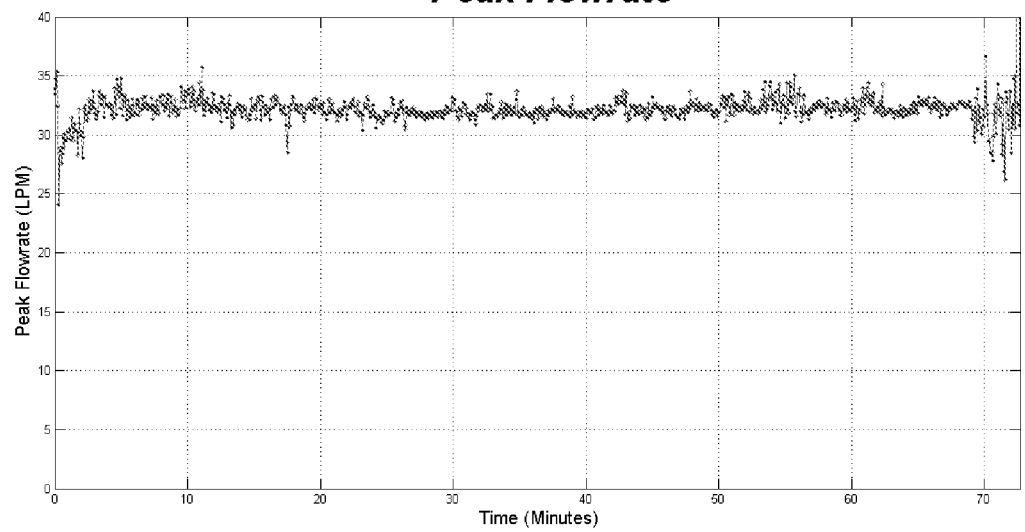
Figure 14F:
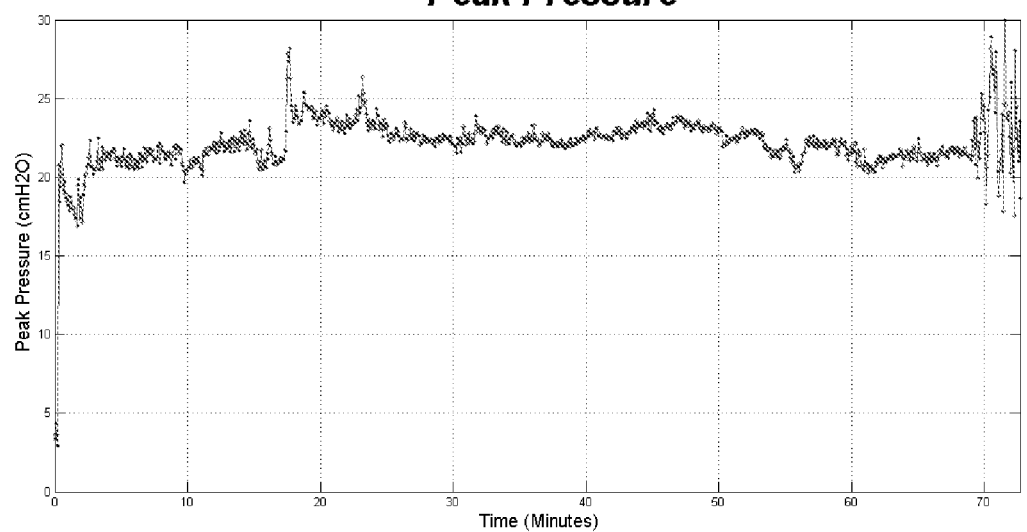

FIGS. 14A, 14B, 14C, 14D, 14E, and 14F show the results from clinical testing of the ventilator shown. FIGS. 14A and 14B show the improvement in control on tidal volume and flow rate, respectively, when the automatic breathing machine is used versus when the ambu bag is manually actuated. FIGS. 14C, 14D, 14E, and 14F represent different parameters measured during field testing. The tidal volume and inhalation time as shown in FIG. 14C and FIG. 14D, respectively, are ventilator-controlled parameters. Peak flowrate and peak pressure as shown in FIG. 14E and FIG. 14F, respectively, are patient dependent and are not controlled by the device. It shows that our ventilator can maintain the tidal volume and inhalation time to the set numbers while the system provides air to an actual patient.

Figure 15A:
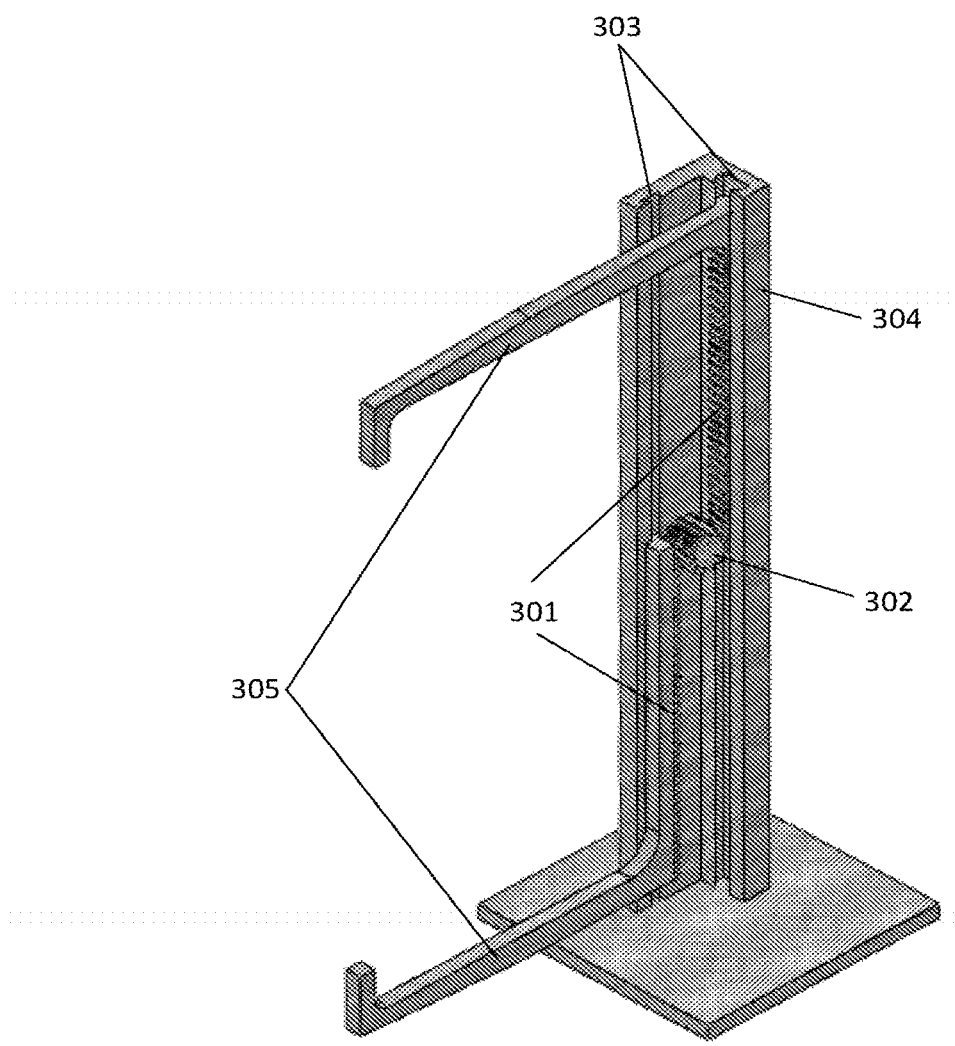
Figure 15B:
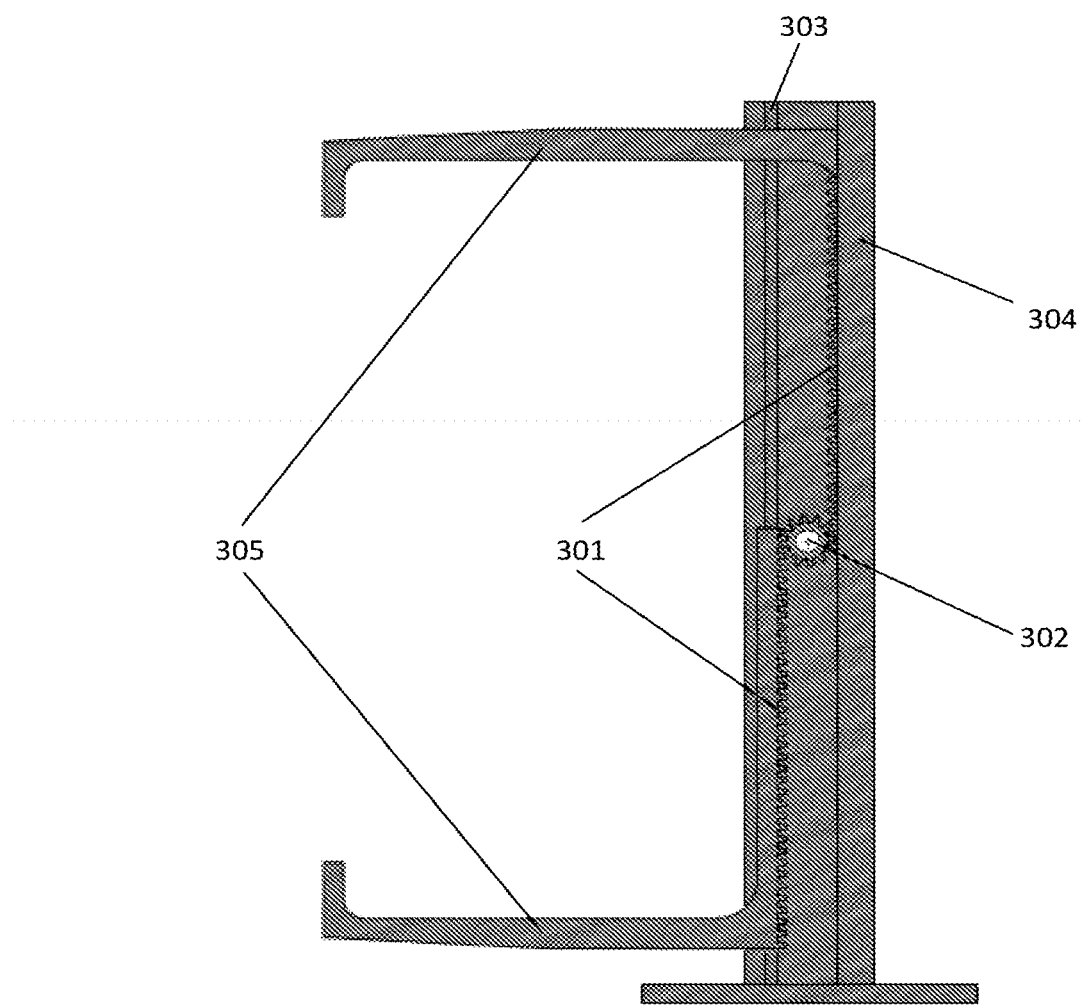

FIG. 15A and FIG. 15B show two different views, i.e., isometric in FIG. 15A and front side in FIG. 15B, of another implementation (SECOND implementation) of the Mechanical Actuation Unit MAU (3). This implementation uses a rack-and-pinion mechanism to press the BVM (4) where two racks (301) are moved to-and-fro by pinion (302) in the machined-slidings (303) which act as sliding bearings for racks. Slidings (303) are machined in a support (304) which holds both racks as well as DC motor (not shown). Pinion is coupled with a DC motor (not shown). The two racks (301) are connected to two jaws (305). Theses jaws (305) then press the Bag Valve Mask (not shown) when racks (301) are forced to move forward by pinion (302) which is being rotating by the DC motor.

Figure 16A:
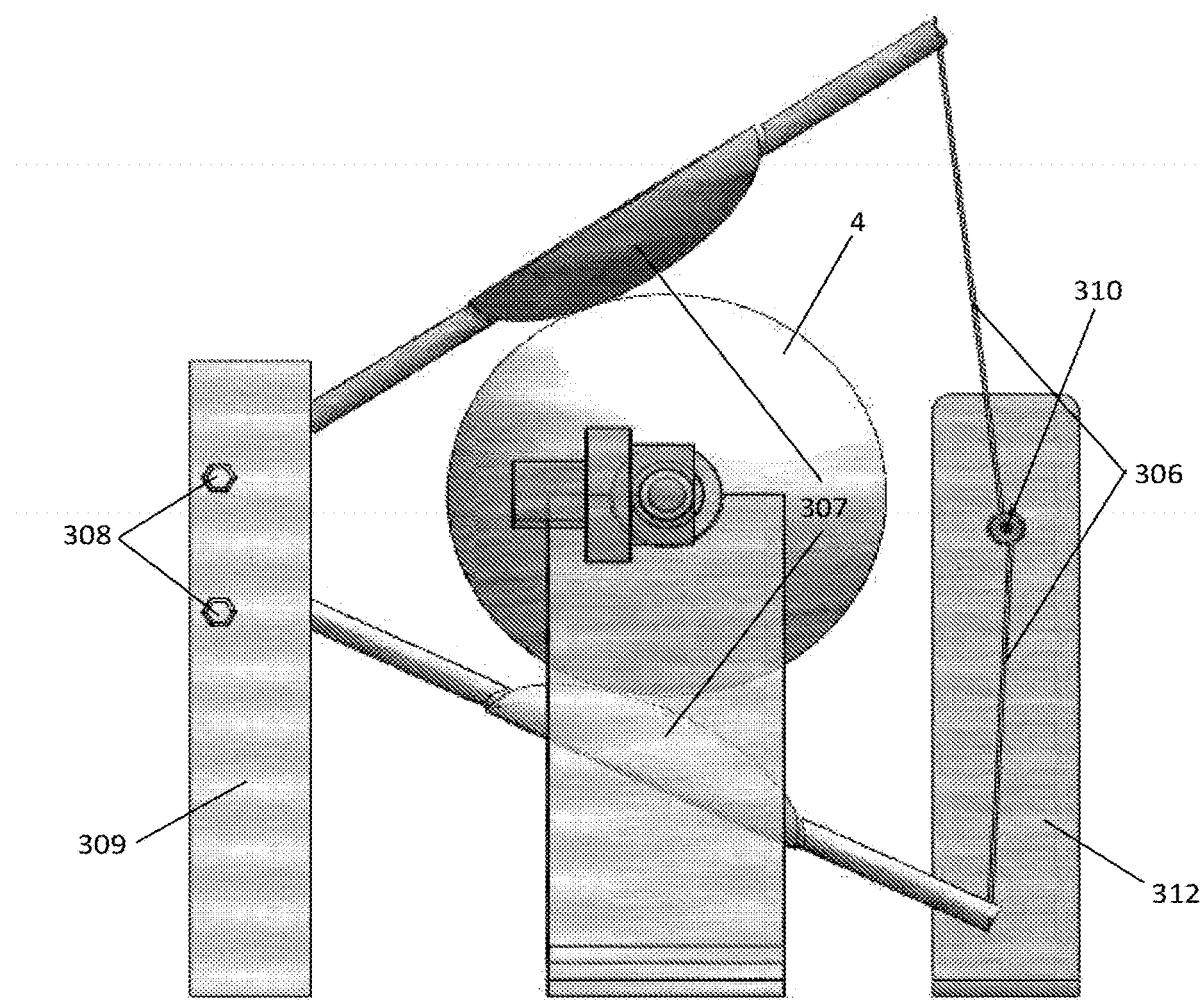
Figure 16B:
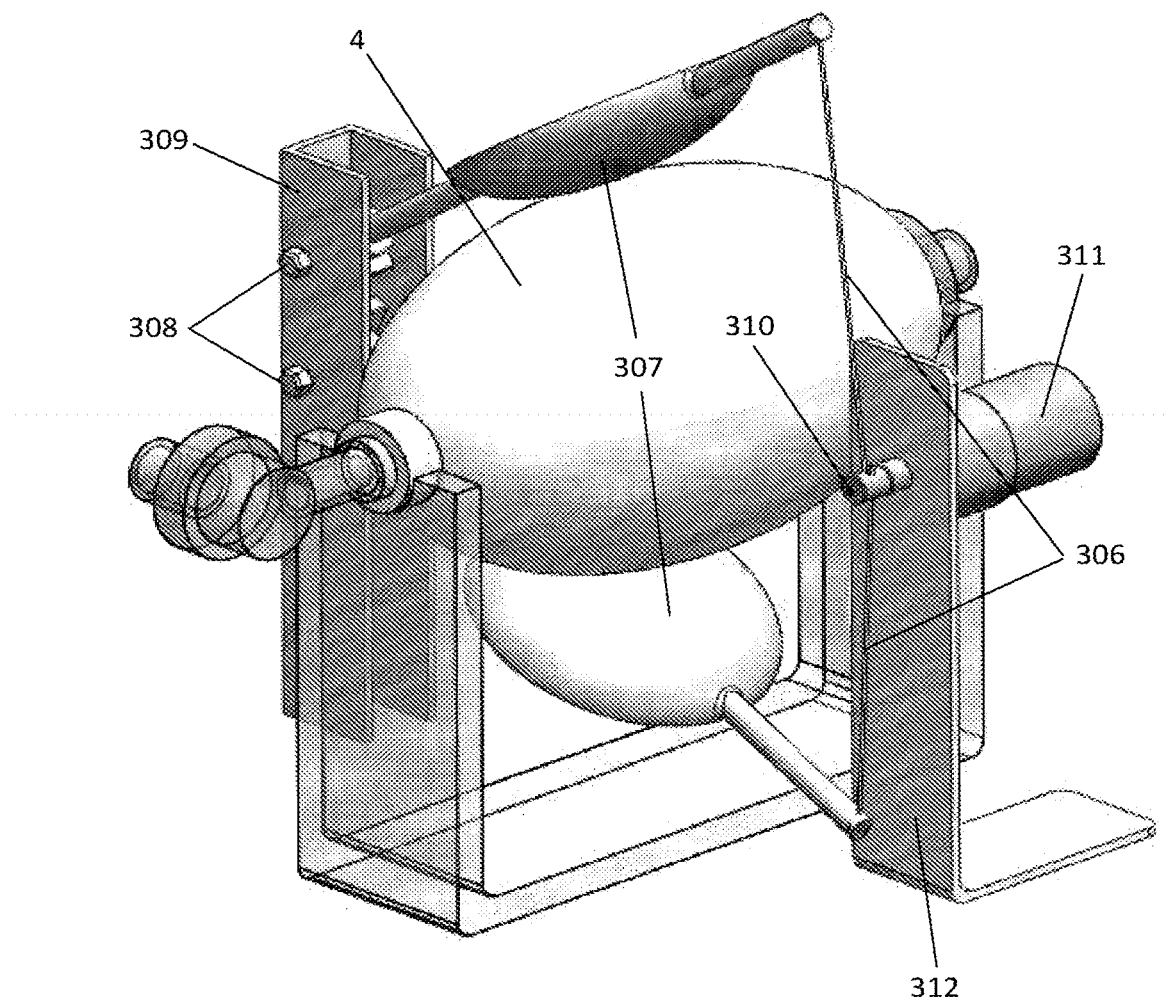

FIG. 16A and FIG. 16B show two different views, i.e., front side in FIG. 16A and isometric in FIG. 16B, of another (THIRD) implementation of the MAU (3). This implementation has rope-pulley mechanism where two ropes (306) connected to two jaws (307) which are pivoted at points (308) on a support (309) with the help of bearings. When the pulley (310) is rotated via a DC motor (311), which is being hold by motor support (312), ropes (306) started to rap on the pulley (310), thus pulling the jaws (307) and compressing the Gas Volume Generator or Bag Valve Mask BVM (4) present between them.

Figure 17:
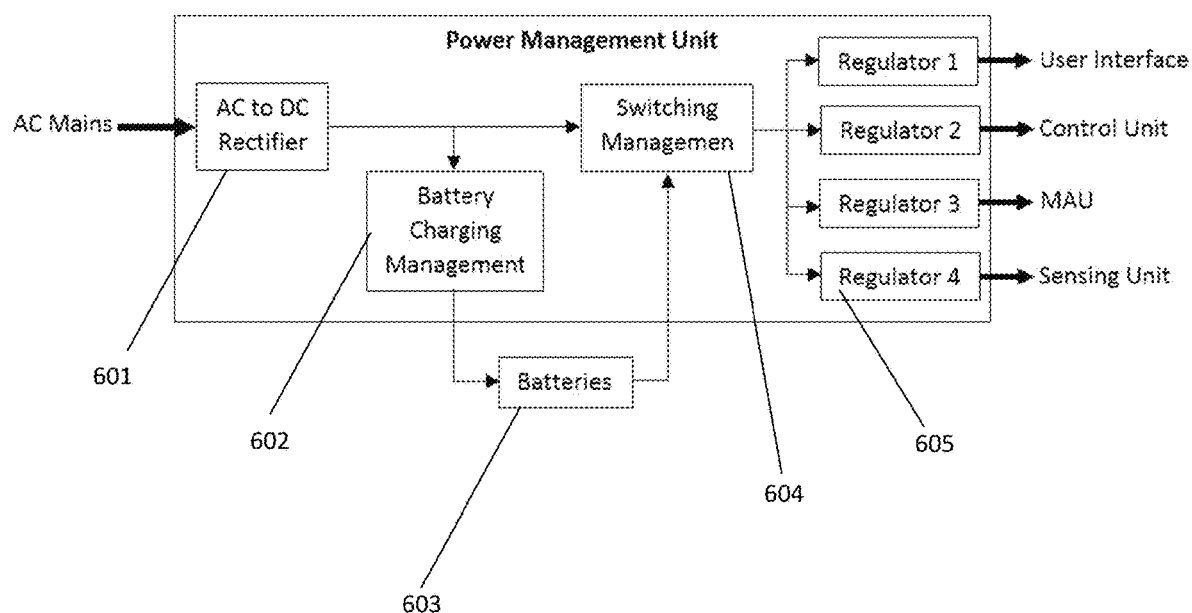

FIG. 17 represents high level diagram of Power Management Unit PMU (6) that regulates power transfer to the entire system. It uses a rectifier (601) to convert AC mains to DC voltage that is then used to power the system and to charge the batteries. Batteries (603) are charged via battery charging management circuit (602). A switching management circuitry (604) ensure uninterrupted power by seamlessly switching between AC mains power source and the battery power. A regulator (605) is used to stabilize the generated DC supply before routing it to power part of a system. Different regulators are used for different system components.

DETAILED DESCRIPTION OF PREFERRED EMBODIMENTS

The design philosophy behind the presented breathing support device is to make a low-cost design that uses already acceptable components which will allow for easy development and regulatory approval. Hence, the main component of the system is the ambu bag or bag valve mask (BVM) which is already used for mechanical respiration. The disclosed system is designed to automate the actuation of the BVM and to regulate its safe use through monitoring of breathing gas flow rate and pressure. It is to be noted that the BVM is one example of gas volume generator (GVG). Other example could be an electrically operated pneumatic pump or a bellow.

The system uses a combination of mechanical components (e.g. for actuation of BVM), electrical components (e.g. for automation for actuation), pneumatic components (e.g. to provide breathing gas). Each part is designed to minimize cost while providing reliability required for medical applications.

The design philosophy for the actuator part of the system is to minimize the number of moving parts in the system and to avoid difficult machining or assembly process. We compared different methods of actuation including electromagnetic actuation using electromagnets, linear actuation using linear actuators, rotary actuation using motors, cam shafts etc. We implemented different mechanisms for actuation and compared their advantages and disadvantages.

The actuation mechanism replicates the manual actuation from human hands as the BVM is designed for manual actuation. One example of mechanical actuation is a pair of rounded metal pieces on top and bottom side of the ambu bag to compress and release it. An electrical motor is used for automation of the actuation process. The mechanical assembly is coupled to the actuation mechanism (e.g. motor) using some sort of circular-to-translinear motion converter. An example is the use of a gear assembly connected with rounded jaws to achieve this (FIG. 10). The motor is also connected with an encoder to provide feedback of its position to the system to compensate for any anomaly or error in the actuation. Different actuation assemblies can be made and tested using rapid prototyping techniques like milling, drilling and CNC.

The electrical part of the system mainly consists of a combination of printed circuit boards. One main board (like a motherboard in a personal computer) is designed to house these printed circuit boards in a modular format. Each board contains the components for a certain function required for system operation. For example, a system control unit (CU) PCB is designed to utilize a high-performance microcontroller (e.g. Arm Cortex M0) for controlling system operation. Another design can use a PIC18F microcontroller along with typical electrical I/O (switches, LEDs, relays, connectors) commonly known to a person skilled in the art as a microcontroller for the CU.

To get desired torque to move the actuation assembly, high current motor drivers are used in a motor driver circuit. Typical current requirements are from 100 mA to 3 A depending upon the motor which in turn depends upon the size of the BVM. The motor drivers use heat sink to minimize thermal damage during use. The motor driver is used between the CU and the motor.

The device is powered by a power management unit (PMU). The PMU is designed like laptop computers i.e. the AC mains power (from wall outlet) is used to power the system as well as to charge system batteries. The backup power source in the form of one or more batteries is useful in case of power interrupts and for portable use as in ambulances and in remote areas with shortage of continuous power supply. Hence, the system is designed to work with both power sources. The system can also be charged by a small portable generator that can run on liquid fuels or operated manually using a rotary or foot peddle. The efficient system design allows for hours of continuous operation with a suitable battery [17]. Normally, two different batteries are used, one (bigger) for the motor and other (smaller) for the rest of the system. Different type of batteries can be used in the system e.g. lead-acid batteries, dry cell batteries. or Lithium polymer (LiPo) batteries. Lead-acid batteries are normally cheaper but heavier and require some maintenance. Dry cell and LiPo batteries are expensive but are lighter and require less maintenance. The unit contains portable batteries with recharging circuitry (e.g. KR-7000F from Panasonic), voltage measurement circuit to determine the requirement of recharging (e.g. STM6904 from ST Microelectronics), and voltage regulators (e.g. ADP150 from Analog Devices) to provide stable voltage to allow for a smooth operation of the entire system. The system uses LEDs and alarms to indicate battery status (e.g. charging level).

The PMU can use both AC mains and internal battery as power source. It uses a rectifier to convert AC mains into DC voltage. This rectified DC voltage is then fed to battery charging management and switching circuitry. If AC mains is available, batteries will be charged by the charging management circuitry. Also, if AC mains is available, switching circuitry will use that to power the system. If AC mains is not available, switching circuitry will switch to using batteries without any interruption. Also, if system is operating on batteries and AC mains becomes available, switching circuitry will switch the system back to AC mains without any interruption and batteries will start to charge. After switching management, DC voltage is stepped-down via voltage regulators and distributed to each module according to its requirements.

For the sensing unit (SU), temperature, pressure, humidity and oxygen sensors are used to ensure safe and accurate operation of the system. A spirometer/flow-rate sensor is used to measure the flow of air provided to the patient. Similarly, a pressure sensor is used to measure the pressure of the air flow to the patient. The pressure depends upon the condition of the patient and the percentage of natural respiration process that may be present. Also, during the course of actual use, patient's self-respiration can change, and sensor feedback is essential to adjust the system accordingly [14]. The design incorporates optional valves to adjust air/oxygen ratio as required in some applications [16]. In some cases, the ratio is automatically selected based upon the house supply and hence is directly used. Humidity is also controlled automatically by passing the air intake through a water/steam chamber. Example of sensors include flow sensors (e.g. HAFUHH0050L4AXT Analog Airflow sensor from Honeywell), Pressure Sensors (SSCSANN001PGAA5 Analog Pressure Sensor from Honeywell) and composition sensors (e.g. Oxygen sensor such as KGZ-10 Series from Honeywell).

The system can also include a wireless interface providing status information to a smart-phone or a similar system. Different algorithms and alarms can be used to process this data allowing direct feedback to the medical practitioner/caregiver. This allows for scaling up this solution for many patients observed by a single medical practitioner (e.g. a Nurse). The data from the ventilators can be processed at individual level to predict patient health patterns and suggest treatment pathways. The data from a larger number of such devices can help in determining trends at population levels and outbreak of epidemics as well as in registering the correct use of such devices and their actual deficiency. It also helps to design a resource management system whereby patients can be directed towards the closest facility with available ventilators so that they don't lose time during travel and figuring out their next possible destination if the patient is in critical need of a ventilator.

The device can use Bluetooth Low energy and Wireless LAN for wireless link with a smart hub within a hospital ward. The central hub can communicate with a smart phone or tablet using WiFi. It can also be used to communicate data to a central service providing availability and usage statistics. The wireless communication scheme uses encryption based upon international standards. User interface design ensures that medical practitioners are able to work with it and are comfortable with it. The unit is implemented by including a wireless connectivity module/chipset in the system. An example is the BLE chipset from microchip (RN4020). The functionality is provided in the form of a wireless connectivity kit that can be connected to a standard port (e.g. serial, usb) available on the electrical circuit board for such functionality.

The presented breathing support device is designed to have a decision-flow architecture (also termed as the software architecture) to run it in different modes. As an example, a typical implementation will have a simple, normal and a smart mode. The simple mode simply automates ambu bag actuation without using any feedback control i.e. it operates in open-loop. It can be used on patients with no effort of their own and provides 'ambu bag like' operation but without the need for a human operator. The normal mode uses the data from different sensors to achieve the desired volume, pressure etc. by considering patient efforts as well. This mode is safer than commonly used ambu bag since it synchronizes the actuation of the ambu bag with patient's breathing pattern to minimize the possibility of pressure build-up that can cause ventilator induced lung injury. In the smart mode, the ventilator uses adaptive learning to adjust its operation based upon a training algorithm that is used to optimize its operation for each patient. The smart mode uses data from all the different sensors used in the ventilator and at exhale and inhale port near the patient. It allows system to converge to optimal flow, pressure and humidity ranges compared to the normal mode. For patients with varying breathing effort, the smart mode is most optimal.

The system uses sensor's feedback and user settings to use one of several different modes. For example, it can use volume-controlled modes mode by integrating the flow rate sensor's data to determine the volume (tidal volume) delivered to the patient. The examples of modes that can be implemented using this technique include continuous mandatory ventilation (CMV), assist-control ventilation (ACV), or synchronous intermittent mandatory ventilation (SIMV). The system uses pressure sensor measurements in this mode to ensure that the system operate within the safety limits. The system can use a Proportional-Integral-Derivative (PID)

controllers to implement all these modes as well as pressure-controlled modes as it provides more control. In advanced implementations, the system can use a machine-learning based approach to adjust its operation to the patient's conditions based upon results gather from large pool pd earlier patient data. This can enable an intelligent use of system that will enable performance levels not obtained from traditional ventilators or ambu bag.

The system can use a humidity and temperature control unit between the system output and the patient, if longer term ventilation is desired. This component essentially uses water to create moisture through which the breathing gas passes. A humidity sensor is used to control the amount of moisture (via heat) and hence the level of humidity in the passing air. Similar mechanism can also be used to adjust the temperature of the breathing gas to be close to body temperature.

We have built our ventilator and have tested it in the field with very good results. Although other portable ventilator designs have been presented before [11], our design utilize unique features consisting of (i) design of mechanical actuation based upon pulley or gear system, (ii) sensing based feedback for an ambu bag based system to enable safe and effective use in different modes, (iii) use of dual power mode to allow the system to run on both AC mains and battery, (iv) use of humidity and temperature control to allow long term use from the otherwise restricted ambu bag based resuscitator, (v) the use of smart algorithms to adjust the operation in run-time, (vi) use of data collection via wireless link to enable remote monitoring enabling smart decision making by medical staff. A comparison of one implementation of the presented device with a commercial system in table I shows the range of different parameters for both. It shows the suitability of the presented system for many cases.

TABLE I

Comparison between the Ambulator and a conventional ICU Ventilator

| Parameter Name | Ambulator Capacity | Typical Value | SERVO-i Capacity | Unit |
| --- | --- | --- | --- | --- |
| Tidal Volume (Vt) | 100 to 800 | 400 | 100 to 4000 | Millileters (mL) |
| Inhalation-Time to Exhalation-Time Ratio (I:E) | 1:1 to 1:4 | 1:2 | 1:1 to 1:4 | Seconds:Seconds |
| Pressure Support | 0 to 50 | 15 | 0 to 120 | Centimeters of Water (cmH2O) |
| Respiratory Rate (RR) | 1 to 25 | 12 | 4 to 150 | Breaths per Minute (BPM) |
| Pressure Triggering | −20 to 0 | −2 | −20 to 0 | Centimeters of Water (cmH2O) |
| Flow Triggering | 0 to 20 | 5 | 0 to 20 | Liters per Minute (LPM) |
| Positive End-Expiratory Pressure (PEEP) | 0 to 50 | 5 | 0 to 50 | Centimeters of Water (cmH2O) |

In summary, we present a unique and innovative design of a low-cost ventilator that is based upon automation of the already accepted manual resuscitator i.e. the ambu bag by using electrical motors and sensors-based feedback control system to provide safe and regulated operation when expensive ventilators aren't available. The system doesn't provide the advanced functions of big ICU ventilators but can provide lifesaving support for majority of cases till the patient recovers or a better alternative becomes available. Hence, it can save thousands of lives each year if used at large scale.

Each of the following References is hereby incorporated by reference herein, in its entirety:

1. http://www.cdc.gov/globalhealth/countries/pakistan/pdf/pakistan_factsheet.pdf
2. http://www.chiesipakistan.com/index.php?page=Respiratory+Diseases
3. http://tribune.com.pk/story/1050073/short-of-facilities-petition-filed-against-pims-over-lack-of-ventilators/
4. 'The epidemiology of mechanical ventilation use in the United States', Wunsch H, Linde-Zwirble W T, Angus D C, Hartman M E, Milbrandt E B, Kahn J M., Crit Care Med. 2010 October; 38(10):194753.
5. 'ICU occupancy and mechanical ventilator use in the United States', Wunsch H, Wagner J, Herlim M, Chong D H, Kramer A A, Halpern S D, Critical Care Med. 2013 December; 41(12):27129
6. 'Systems for the management of respiratory disease in primary care—an international series: Pakistan', Yusuf M O, Prim Care Respir J. 2009 March; 18(1):3-9
7. 'Local Production and Technology Transfer to Increase Access to Medical Devices. Addressing the barriers and challenges in low- and middle-income countries', World Health Organization, 2015
8. 'Building a Reliable Wireless Medical Device Network', David Hoglund and Vince Varga, BEST PRACTICES
9. 'Medical Devices Making in India—A Leap for Indian Healthcare', Deloitte Research report
10. 'Development of Field Portable Ventilator Systems for Domestic and Military Emergency Medical Response', Charles W. Kerechanin I I, Protagoras N. Cutchis, Jennifer A. Vincent, Dexter G. Smith, and Douglas S. Wenstrand, JOHNS HOPKINS APL TECHNICAL DIGEST, VOLUME 25, NUMBER 3 (2004)
11. 'Design and Prototyping of a Low-cost Portable Mechanical Ventilator', Abdul Mohsen Al Husseini et al., Proceedings of the 2010 Design of Medical Devices Conference, Apr. 13-15, 2010, Minneapolis, Minn., USA
12. 'Sensors and Flexible Heaters in Ventilator Applications', Honeywell Application Note
13. 'Ventilator/Respirator Hardware and Software Design Specification', Freescale Technical Document Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

The invention claimed is:

1. A method of controlling a gas flow from a bag valve mask to a patient through a patient interface comprising:
   connecting a flow rate sensor and a pressure sensor to the bag valve mask and the patient interface;
   connecting a valve to the patient interface;
   positioning a mechanical actuation unit adjacent to the bag valve mask;
   determining a status of gas flow using sensor readings from at least the flow sensor and the pressure sensor;
   automatically matching a compression of the bag valve mask by the mechanical actuation unit to a breathing cycle of the patient;
   automatically releasing the bag valve mask once a desired volume of gas is delivered or once reaching a pressure above a predetermined threshold; and
   automatically closing the valve upon detection of a pressure below a set positive-end-expiratory-pressure (PEEP).

2. The method of claim 1, wherein the gas flow is controlled to provide one of the following volume-controlled modes: assist-control ventilation (ACV) or synchronous intermittent mandatory ventilation (SIMV), both while maintaining the pressure below the safety limit.

3. The method of claim 1, wherein the gas flow is controlled to provide a pressure-controlled ventilation mode.

4. The method of claim 1, wherein the range of pressure is 0 cmH$_2$O to 120 cmH$_2$O.

5. The method of claim 1, wherein the inhalation to exhalation Ratio (I:E) is controlled in clinically relevant range 4:1 to 1:4.

6. The method of claim 1 further comprising the activation of a smart mode, wherein the readings from the pressure sensor and the flow sensor are inputted into an adaptive learning program based upon a training algorithm to optimize gas flow for a patient.

7. The method of claim 1 further comprising connecting a humidity and temperature control unit to control the temperature of the gas and the amount of moisture in the gas provided to the patient.

8. The method of claim 1 wherein the mechanical actuation unit is an electrical motor to mechanically actuate a pair of opposing members to put the bag valve mask in a compressed or uncompressed state.

9. The method of claim 8 wherein the pair of opposing members are jaws.

10. The method of claim 8 further comprising connecting the electrical motor, patient interface, valve, and bag valve mask to a power source in the form of one or more batteries.

11. The method of claim 8 further comprising connecting the electrical motor, patient interface, valve, and bag valve mask to a power source in the form of AC mains power.

12. The method of claim 1 wherein the valve is a solenoid valve.

13. The method of claim 1 further comprising connecting a second valve to the bag valve mask and patient interface to adjust an air-oxygen ratio of the gas flow.

14. A method of controlling a gas flow from a bag valve mask comprising:
   connecting a flow rate sensor and a pressure sensor to the bag valve mask and a patient interface;
   continuously determining the status of the gas flow using readings from the flow sensor and the pressure sensor;
   connecting a valve to the bag valve mask and the patient interface to control pressure in the patient, said valve automatically opening upon detection of a pressure at least equal to a maximum pressure and automatically closing when pressure is below a minimum pressure;
   synchronizing a compression of the bag valve mask to an inhalation of the patient by automatically triggering said compression upon the evaluation of an inhalation criteria to minimize pressure build up, said inhalation criteria comprising:
      passage of a predetermined time period; and
      detection of a pressure drop below a predetermined threshold;
   synchronizing a release of the bag valve mask to an exhalation of the patient by automatically triggering said release upon the evaluation of an exhalation criteria, said exhalation criteria comprising:
      delivery of a desired volume of gas; and
      detection of a pressure gradient above a predetermined threshold;
   measuring an exhaling pressure to determine an extent of pressure build-up in the patient; and
   synchronizing compressions and releases of the bag valve mask in subsequent breathing cycles to keep an internal pressure below a safety limit.

* * * * *